(12) United States Patent
Dadd et al.

(10) Patent No.: US 9,101,732 B2
(45) Date of Patent: Aug. 11, 2015

(54) DRUG-DELIVERY ACCESSORY FOR AN IMPLANTABLE MEDICAL DEVICE

(71) Applicants: Fysh Dadd, Lane Cove (AU); Jane Rapsey, Berowra (AU); Peter Gibson, South Coogee (AU); Peter Schuller, Turramurra (AU); Carrie Newbold, Richmond (AU)

(72) Inventors: Fysh Dadd, Lane Cove (AU); Jane Rapsey, Berowra (AU); Peter Gibson, South Coogee (AU); Peter Schuller, Turramurra (AU); Carrie Newbold, Richmond (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 14/108,809

(22) Filed: Dec. 17, 2013

(65) Prior Publication Data

US 2014/0180195 A1    Jun. 26, 2014

Related U.S. Application Data

(62) Division of application No. 12/786,313, filed on May 24, 2010, now Pat. No. 8,617,097.

(51) Int. Cl.
*A61M 31/00* (2006.01)
*A61M 25/00* (2006.01)
*A61K 9/00* (2006.01)
*A61M 37/00* (2006.01)
*A61N 1/05* (2006.01)

(52) U.S. Cl.
CPC .............. *A61M 25/00* (2013.01); *A61K 9/0009* (2013.01); *A61K 9/0024* (2013.01); *A61K 9/0046* (2013.01); *A61M 31/002* (2013.01); *A61M 37/0069* (2013.01); *A61N 1/0541* (2013.01)

(58) Field of Classification Search
CPC ... A61N 1/0541; A61N 1/36032; A61N 1/05; A61N 1/32; A61N 1/36; A61N 1/37229; A61L 2430/14; A61M 25/00; A61M 2210/0668; A61M 31/002; A61M 5/14276; A61M 2210/0662; A61M 31/00; A61K 9/0046; A61K 9/0009; A61K 9/0024
USPC ........................................................ 604/57
See application file for complete search history.

(56) References Cited

U.S. PATENT DOCUMENTS 3,890,977 A    6/1975  Wilson
4,046,151 A    9/1977  Rose
4,154,247 A    5/1979  O'Neill
(Continued)

FOREIGN PATENT DOCUMENTS

DE    100 32 0000 A1    1/2001
EP    0 002 068 A2    5/1979
(Continued)

OTHER PUBLICATIONS

English Translation of Office Action in Chinese Application No. 201180036177.1, mailed Feb. 27, 2015, 4 pages.
(Continued)

*Primary Examiner* — Jason Flick

(57) ABSTRACT

An implantable drug-delivery sleeve for an elongate component of an implantable medical device. The sleeve includes a tubular substrate having a lumen configured to receive the elongate component so as to allow relative displacement of the substrate and the elongate component, wherein the substrate is shaped so as to be retained stationary at a desired position along the elongate component, and a drug releasably carried by the substrate.

21 Claims, 11 Drawing Sheets

(56) References Cited

U.S. PATENT DOCUMENTS

| | | | |
|---|---|---|---|
| 4,306,563 A | 12/1981 | Iwatschenko | |
| 4,351,337 A | 9/1982 | Sidman | |
| 4,357,479 A | 11/1982 | Imai | |
| 4,357,497 A | 11/1982 | Hochmair et al. | |
| 4,381,013 A | 4/1983 | Dutcher | |
| 4,506,680 A | 3/1985 | Stokes | |
| 4,532,930 A | 8/1985 | Crosby et al. | |
| 4,762,135 A | 8/1988 | van der Puije et al. | |
| 4,784,161 A | 11/1988 | Skalsky et al. | |
| 4,819,662 A | 4/1989 | Heil, Jr. et al. | |
| 4,844,099 A | 7/1989 | Skalsky et al. | |
| 4,972,848 A | 11/1990 | Di Domenico et al. | |
| 4,994,069 A | 2/1991 | Ritchart et al. | |
| 5,066,278 A | 11/1991 | Hirschberg et al. | |
| 5,092,332 A | 3/1992 | Lee et al. | |
| 5,262,608 A | 11/1993 | Mustonen | |
| 5,458,631 A | 10/1995 | Xavier | |
| 5,474,542 A | 12/1995 | Gandi et al. | |
| 5,531,780 A | 7/1996 | Vachon | |
| 5,554,114 A | 9/1996 | Wallace et al. | |
| 5,645,585 A | 7/1997 | Kuzma | |
| 5,653,742 A * | 8/1997 | Parker et al. | 607/137 |
| 5,697,951 A | 12/1997 | Harpstead et al. | |
| 5,755,474 A | 5/1998 | Slomski | |
| 5,755,765 A | 5/1998 | Hyde et al. | |
| 5,769,077 A | 6/1998 | Lindegren | |
| 5,782,744 A | 7/1998 | Money | |
| 5,800,500 A | 9/1998 | Spelman et al. | |
| 5,902,329 A | 5/1999 | Hoffmann et al. | |
| 5,929,041 A | 7/1999 | Magal | |
| 5,975,085 A | 11/1999 | Rise | |
| 6,038,482 A | 3/2000 | Vachon | |
| 6,038,483 A | 3/2000 | KenKnight et al. | |
| 6,038,484 A | 3/2000 | Kuzma | |
| 6,078,841 A | 6/2000 | Kuzma | |
| 6,119,044 A | 9/2000 | Kuzma | |
| 6,125,302 A | 9/2000 | Kuzma | |
| 6,163,729 A | 12/2000 | Kuzma | |
| 6,259,951 B1 | 7/2001 | Kuzma et al. | |
| 6,304,787 B1 | 10/2001 | Kuzma et al. | |
| 6,309,410 B1 | 10/2001 | Kuzma et al. | |
| 6,321,125 B1 | 11/2001 | Kuzma | |
| 6,398,758 B1 | 6/2002 | Jacobsen et al. | |
| 6,421,569 B1 | 7/2002 | Treaba et al. | |
| 6,889,092 B2 | 5/2005 | Zhu et al. | |
| 6,936,040 B2 | 8/2005 | Kramm et al. | |
| 7,044,942 B2 | 5/2006 | Jolly et al. | |
| 7,206,639 B2 | 4/2007 | Jacobsen et al. | |
| 7,272,449 B2 | 9/2007 | Dadd et al. | |
| 7,571,012 B2 | 8/2009 | Gibson | |
| 8,133,215 B2 | 3/2012 | Gibson | |
| 8,190,271 B2 | 5/2012 | Overstreet et al. | |
| 2002/0032477 A1 | 3/2002 | Helmus et al. | |
| 2002/0077685 A1 | 6/2002 | Sundquist et al. | |
| 2003/0045921 A1 | 3/2003 | Dadd et al. | |
| 2003/0097121 A1 | 5/2003 | Jolly et al. | |
| 2003/0181967 A1 | 9/2003 | Dadd et al. | |
| 2004/0030376 A1 | 2/2004 | Gibson et al. | |
| 2004/0078057 A1 | 4/2004 | Gibson | |
| 2004/0116995 A1 | 6/2004 | Dadd | |
| 2004/0122501 A1 | 6/2004 | Dadd et al. | |
| 2005/0177118 A1 | 8/2005 | Hoganson et al. | |
| 2005/0256560 A1 | 11/2005 | Lenarz et al. | |
| 2006/0264897 A1 | 11/2006 | Lobl et al. | |
| 2006/0287689 A1 * | 12/2006 | Debruyne et al. | 607/57 |
| 2007/0038278 A1 | 2/2007 | Zarembo | |
| 2007/0184085 A1 | 8/2007 | Radhakrishnan et al. | |
| 2007/0287984 A1 | 12/2007 | Lobl et al. | |
| 2008/0033520 A1 | 2/2008 | Jolly | |
| 2008/0152694 A1 | 6/2008 | Lobl et al. | |
| 2008/0262630 A1 | 10/2008 | Fulmer et al. | |
| 2009/0048580 A1 | 2/2009 | Gibson | |
| 2009/0062896 A1 | 3/2009 | Overstreet et al. | |
| 2009/0076581 A1 | 3/2009 | Gibson | |
| 2009/0292237 A1 | 11/2009 | Overstreet et al. | |
| 2009/0292329 A1 | 11/2009 | Gibson | |
| 2011/0288500 A1 | 11/2011 | Dadd et al. | |

FOREIGN PATENT DOCUMENTS

| | | |
|---|---|---|
| EP | 0 007 157 A2 | 1/1980 |
| EP | 0 350 188 A1 | 1/1990 |
| EP | 0 602 859 A2 | 6/1994 |
| EP | 0 653 223 A2 | 5/1995 |
| EP | 0 706 807 A2 | 4/1996 |
| EP | 0 739 642 A2 | 10/1996 |
| EP | 0 773 037 A2 | 5/1997 |
| EP | 0 778 043 A1 | 6/1997 |
| EP | 0 778 044 A2 | 6/1997 |
| EP | 0 778 044 A3 | 7/1997 |
| EP | 0 783 900 A2 | 7/1997 |
| EP | 0 784 994 A1 | 7/1997 |
| EP | 0 784 995 A1 | 7/1997 |
| EP | 0 919 254 A2 | 6/1999 |
| EP | 0 783 901 B1 | 4/2003 |
| EP | 1 604 626 A2 | 12/2005 |
| EP | 2 047 884 A1 | 4/2009 |
| EP | 2047884 A1 | 4/2009 |
| GB | 2 217 993 A | 11/1989 |
| JP | 55-190 A | 1/1980 |
| JP | 08-229137 | 9/1996 |
| JP | 09-508054 T | 8/1997 |
| JP | 11-514252 T | 12/1999 |
| WO | 96/15665 A2 | 5/1996 |
| WO | 97/10784 A1 | 3/1997 |
| WO | 99/00067 A1 | 1/1999 |
| WO | 99/11321 A1 | 3/1999 |
| WO | 99/55360 A1 | 11/1999 |
| WO | 00/56399 A1 | 9/2000 |
| WO | 00/57949 A1 | 10/2000 |
| WO | 00/71063 A1 | 11/2000 |
| WO | 01/41674 A1 | 6/2001 |
| WO | 01/97908 A2 | 12/2001 |
| WO | 02/24064 A1 | 3/2002 |
| WO | 02/32498 A1 | 4/2002 |
| WO | 02/41666 A1 | 5/2002 |
| WO | 02/055136 A2 | 7/2002 |
| WO | 02/083234 A1 | 10/2002 |
| WO | 02/087681 A2 | 11/2002 |
| WO | 03/049658 A1 | 6/2003 |
| WO | 03/072193 A1 | 9/2003 |
| WO | 2009/067764 A1 | 6/2009 |
| WO | 2009067764 A1 | 6/2009 |
| WO | 2009/124041 A1 | 10/2009 |
| WO | 2010/045432 A2 | 4/2010 |
| WO | 2011/148316 A2 | 12/2011 |
| WO | 2011/148317 A2 | 12/2011 |
| WO | 2011/148316 A3 | 4/2012 |
| WO | 2011/148317 A3 | 4/2012 |

OTHER PUBLICATIONS

"Lumen", Merriam Webster, An Encyclopedia Britannica Company, Retrieved on Mar. 28, 2011, Document Available at: < http.//www.merriam-webster.com/dictionary/lumen>.

European Application No. 08253298.7, Office Action mailed on Nov. 6, 2009, 1 Page.

European Application No. 08253298.7, Office Action mailed on Jul. 14, 2010, 3 Pages.

Altschuler et al., "Rescue and Regrowth of Sensory Nerves Following Deafferentation by Neurotrophic Factors", Annals New York Academy of Sciences, Nov. 28, 1999, 884, pp. 305-311.

Australian Application No. 2002223270, First Examination Report mailed on Aug. 17, 2005.

Australian Application No. 2003283124, First Examination Report mailed on Jun. 13, 2008.

Canadian Application No. 2,428,542, Office Action mailed on May 15, 2009.

European Application No. 01973835.0, Supplemental Search Report mailed on Jan. 22, 2004, 3 Pages.

European Application No. 01994538, Examination Report mailed on Apr. 20, 2007, 4 Pages.

(56) References Cited

OTHER PUBLICATIONS

European Application No. 01994538, Supplementary Search Report mailed on May 27, 2005, 3 Pages.
European Application No. 03702212, Examination Report mailed on Jul. 8, 2008, 5 Pages.
European Application No. 03702212, Supplementary Partial Search Report mailed on Jun. 23, 2006, 4 Pages.
European Application No. 08253298.7, Search Report mailed on Jan. 14, 2009, 5 Pages.
Japanese Application No. 2002-543261, Office Action mailed on Jan. 9, 2007.
International Application No. PCT/AU2001/001479, International Preliminary Examination Report mailed on Oct. 4, 2002, 10 Pages.
International Application No. PCT/AU2001/001479, International Search Report mailed on Dec. 3, 2001, 3 Pages.
International Application No. PCT/AU2001/01230, International Preliminary Examination Report mailed on Nov. 27, 2001, 3 Pages.
International Application No. PCT/AU2001/01230, International Search Report mailed on Oct. 26, 2001, 3 Pages.
International Application No. PCT/AU2001/01232, International Preliminary Examination Report mailed on Feb. 25, 2002, 3 Pages.
Inteational Application No. PCT/AU2001/01232, International Search Report mailed on Oct. 26, 2001, 2 Pages.
International Application No. PCT/AU2003/000248, International Preliminary Examination Report mailed on Jun. 2, 2004, 4 Pages.
International Application No. PCT/AU2003/000248, International Search Report mailed on Apr. 7, 2003, 3 Pages.
International Application No. PCT/AU2003/001584, International Preliminary Examination Report mailed on Mar. 15, 2005, 6 Pages.
International Application No. PCT/AU2003/001584, International Search Report mailed on Apr. 2, 2004, 3 Pages.
International Application No. PCT/IB2011/052261, International Search Report and Written Opinion mailed on Feb. 29, 2012, 3 Pages.
International Application No. PCT/IB2011/052262, International Search Report and Written Opinion mailed on Feb. 29, 2012, 3 Pages.
Inteational Application No. PCT/US2009/038942, International Search Report mailed on May 28, 2009, 2 Pages.
International Application No. PCT/US2009/038942, Written Opinion mailed on May 28, 2009, 11 Pages.
International Application No. PCT/AU2001/01231, International Search Report mailed on Oct. 26, 2001, 3 Pages.
PR 0541, Australian Search Report mailed on Dec. 20, 2000.
PR 0542, Australian Search Report mailed on Dec. 20, 2000.
PR 0807, Australian Search Report mailed on Dec. 20, 2000.
Examination Report in European Application No. 11786217.7, mailed Mar. 23, 2015, 5 Pages.
Extended European Search Report in European Application No. 11786218.5, mailed Jul. 9, 2014, 8 pages.
Extended European Search Report in European Application No. 11786217.7, mailed Apr. 10, 2014, 7 pages.
English Translation of Office Action in Chinese Application No. 201180036177.1, mailed Jul. 2, 2014, 13 pages.
Office Action in counterpart European Application No. 11786218.5, dated Jun. 2, 2015, 4 pages.

* cited by examiner

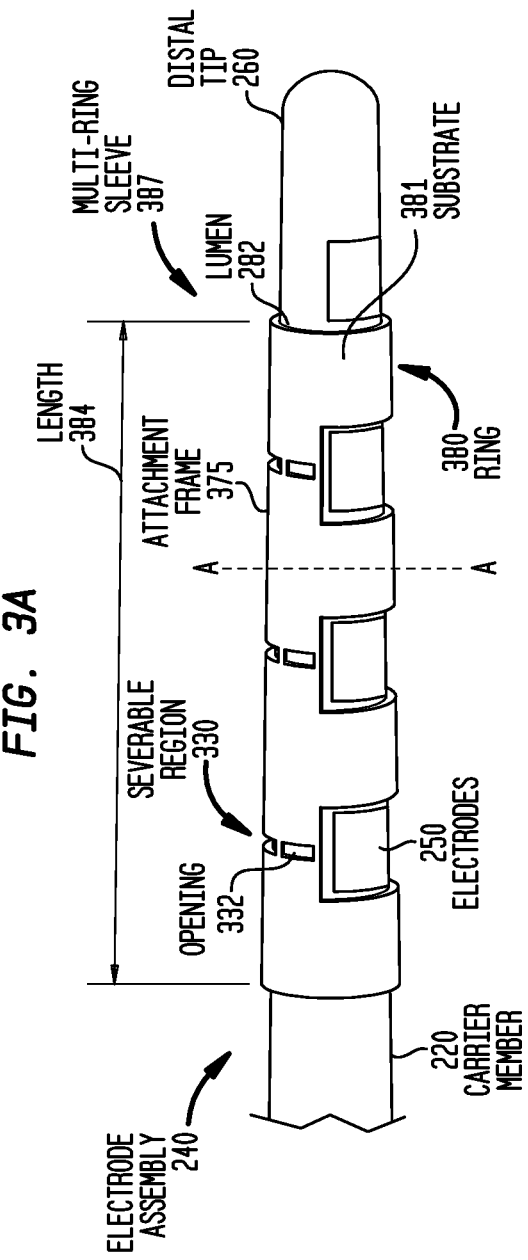
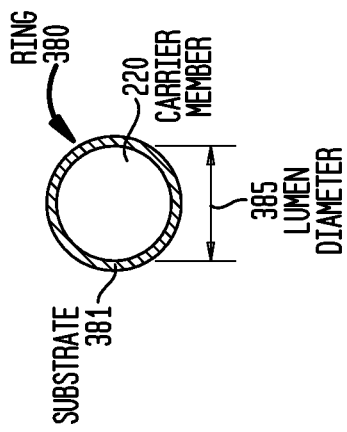
FIG. 3A
FIG. 3B

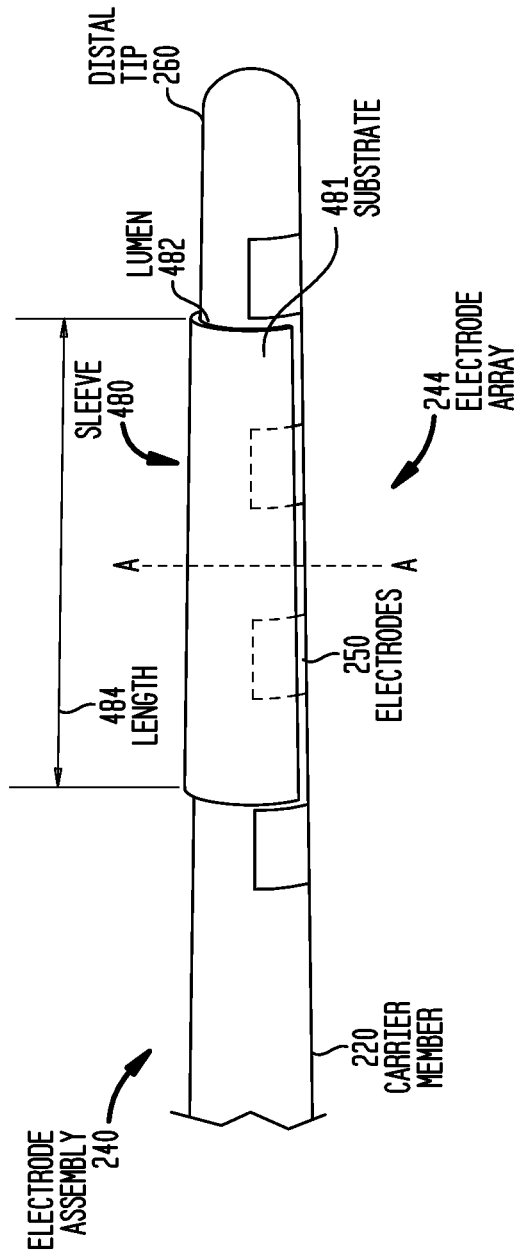
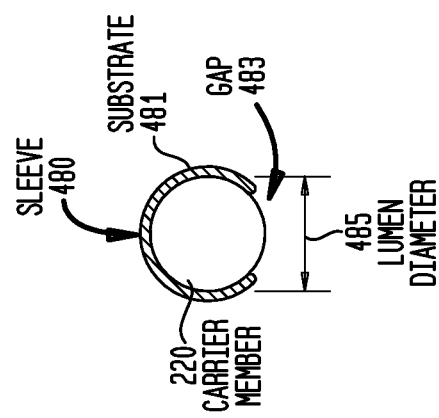
FIG. 4A
FIG. 4B

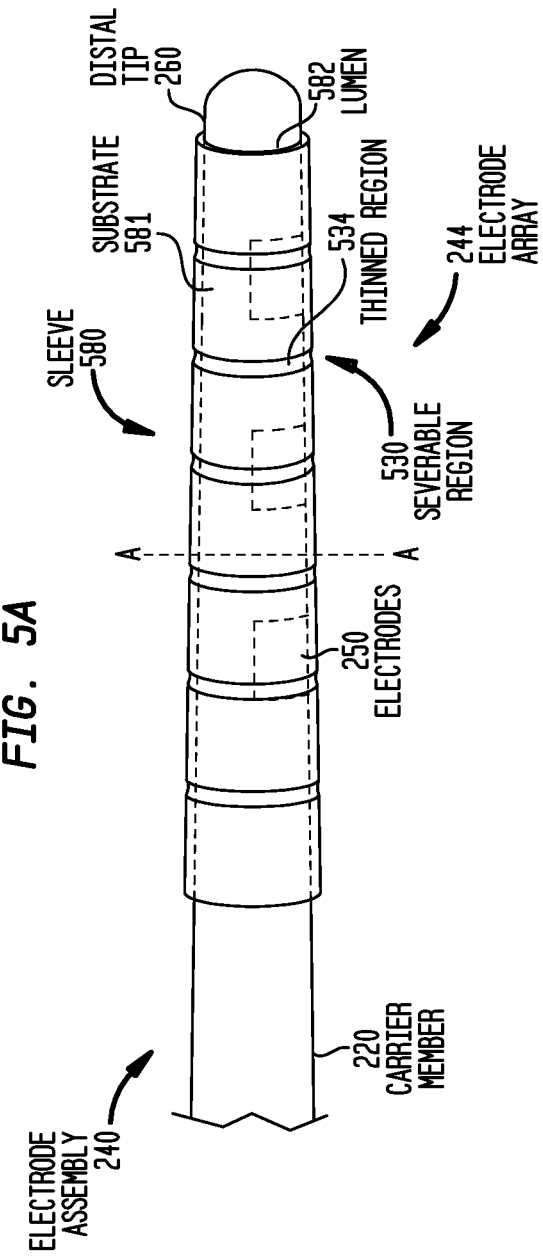
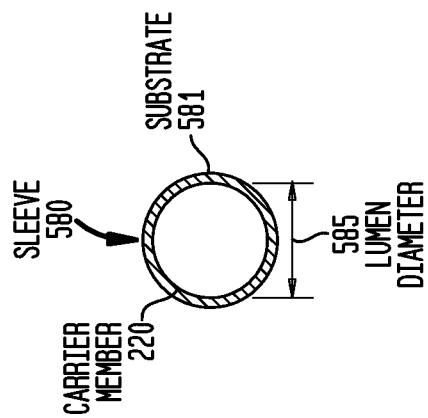

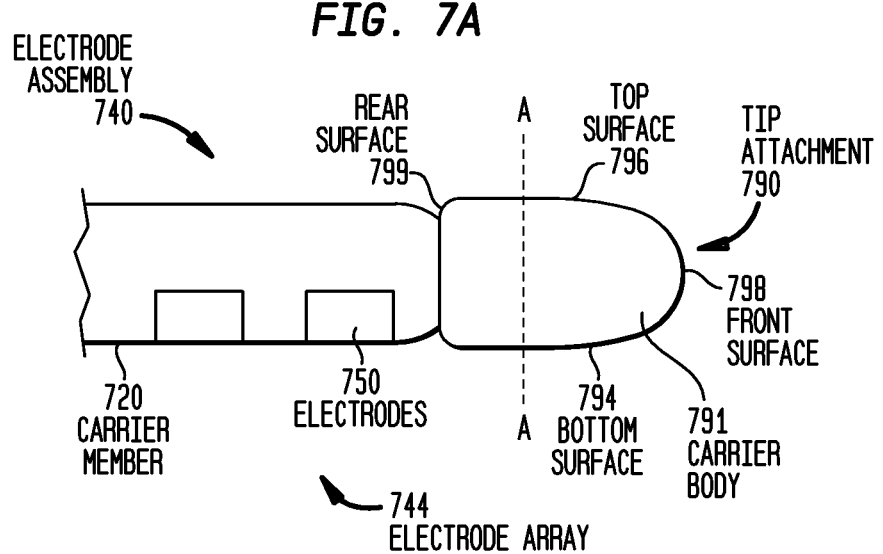
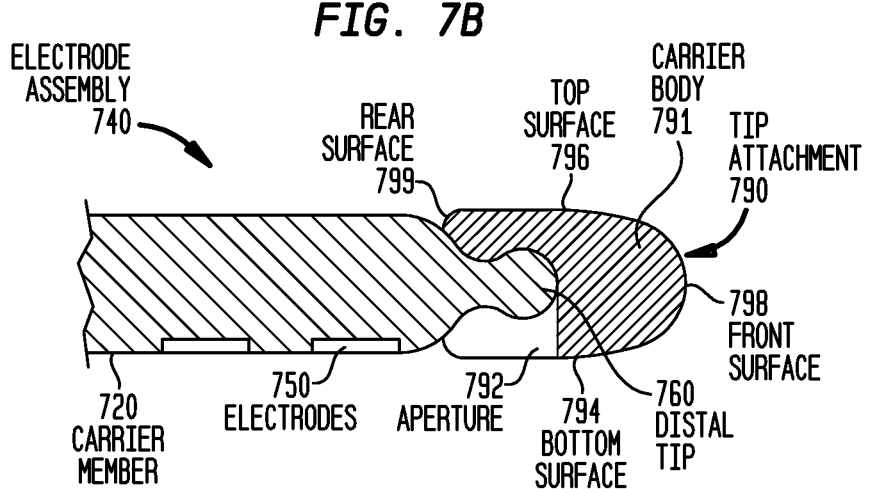
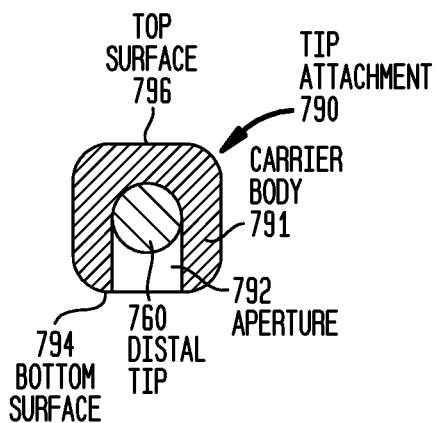

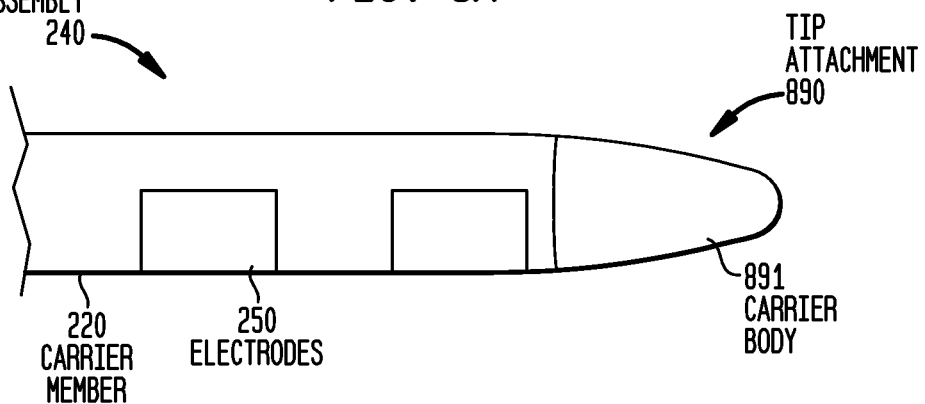
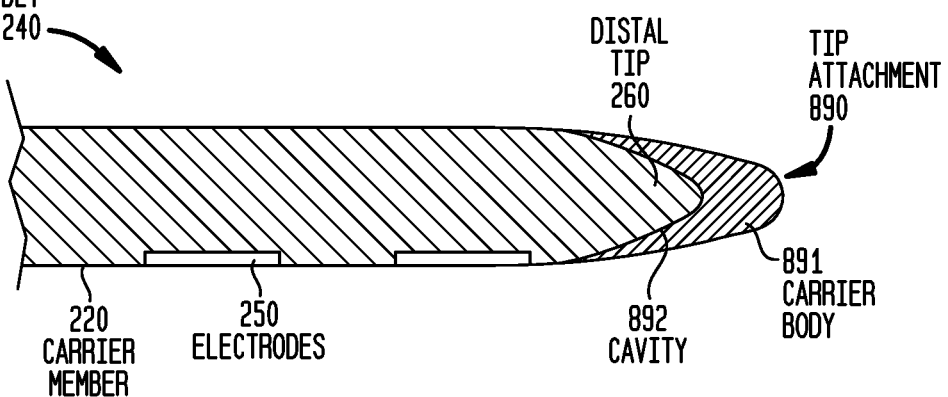

DRUG-DELIVERY ACCESSORY FOR AN IMPLANTABLE MEDICAL DEVICE

CROSS-REFERENCE TO RELATED APPLICATIONS

This application is a divisional application of U.S. patent application Ser. No. 12/786,313, entitled "Drug-Delivery Accessory for an Implantable Medical Device," filed on May 24, 2010, now U.S. Pat. No. 8,617,097 which is hereby incorporated by reference herein in its entirety.

BACKGROUND

1. Field of the Invention

The present invention relates generally to drug-delivery accessories for an implantable medical device, and more particularly, to independently-manufactured and physically distinct drug-delivery accessories for an implantable medical device.

2. Related Art

Medical devices having one or more implantable components, generally referred to herein as implantable medical devices, have provided a wide range of therapeutic benefits to patients (sometimes referred to herein as recipients) over recent decades. Some implantable medical devices include an implantable elongate component that itself performs a therapeutic function, or serves as a carrier for devices that perform such function. Such devices include, for example, devices that perform imaging, detection of physiological conditions, delivery of drugs, application of electrical stimulation, and so on. For example, cochlear implants include an elongate component configured to apply stimulation to a recipient and/or receive signals from a recipient's tissue.

Traditionally, there has been interest in delivering bioactive substances or chemicals (generally and collectively referred to herein as "drugs") in conjunction with a cochlear implant and other implantable medical device. In one conventional drug delivery approach, the implantable medical device is coated with a bioactive substance. In another conventional approach, a bioactive substance is integrated into the polymeric coating of the implantable medical device. These and other conventional approaches typically require the incorporation of the drug into the implantable medical device during the manufacturing process of the device. This introduces a number of difficult problems and challenges for the manufacturing and sterilization processes, particularly for complex implantable medical devices. In other conventional drug delivery approaches, liquid drugs are contained in an external or implanted reservoir and are transferred to a target location in a patient.

SUMMARY

In one aspect of the present invention, an implantable drug-delivery sleeve for an elongate component of an implantable medical device is provided. The drug-delivery sleeve comprises a tubular substrate having a lumen configured to receive the elongate component so as to allow relative displacement of the substrate and the elongate component, wherein the substrate is shaped so as to be retained stationary at a desired position along the elongate component, and a drug releasably carried by the substrate.

In another aspect of the present invention, a kit of implantable drug-delivery sleeves for a tapered elongate component of an implantable medical device is provided. The kit comprises one or more first drug-delivery sleeves, and one or more second drug-delivery sleeves, wherein each of the first and second sleeves comprises a substrate releasably carrying at least one drug and having a lumen configured to receive the elongate component so as to allow relative displacement of the substrate and the elongate component, and wherein the substrate is shaped so as to be retained stationary at a desired position along the elongate component. The first and second sleeves differ in one or more characteristics selected from the group comprising the at least one drug releasably carried by the sleeves, a dosage of the at least one drug, resorbability, and lumen diameter.

In another aspect of the present invention, an implantable medical device is provided. The device comprises an elongate component that is implantable in a recipient, and a drug-delivery sleeve releasably carrying at least one drug and having a lumen configured to receive the elongate component so as to allow relative displacement of the sleeve and the elongate component, wherein the sleeve is manually compressible to the elongate component such that the sleeve is retained stationary relative to the elongate component.

In another aspect of the present invention, an implantable drug-delivery tip attachment for an elongate component of an implantable medical device is provided. The elongate component has a proximal end and a distal tip. The tip attachment comprises a carrier body having a recess configured to receive at least a portion of the distal tip such that the tip attachment may be secured to the elongate component within the recess, and a drug releasably carried by the tip attachment.

In another aspect of the present invention, an implantable medical device is provided. The implantable medical device comprises an elongate component having a proximal end and a distal tip, wherein the elongate component is implantable in a recipient, and a drug-delivery tip attachment configured to be secured to the distal tip of the elongate component, wherein the tip attachment releasably carries at least one drug.

BRIEF DESCRIPTION OF THE DRAWINGS

Illustrative embodiments of the present invention are described herein with reference to the accompanying drawings, in which:

FIG. 3A is a side perspective view of a drug-delivery sleeve disposed on a carrier member, in accordance with embodiments of the present invention;

FIG. 3B is a cross-sectional view of the carrier member and the drug-delivery sleeve of FIG. 3A through a line A-A of FIG. 3A, in accordance with embodiments of the present invention;

FIG. 4A is a side perspective view of a drug-delivery sleeve disposed on a carrier member, in accordance with embodiments of the present invention;

FIG. 4B is a cross-sectional view of the carrier member and the sleeve of FIG. 4A through a line A-A of FIG. 4A, in accordance with embodiments of the present invention;

FIG. 5A is a side perspective view of a drug-delivery sleeve, in accordance with embodiments of the present invention;

FIG. 5B is a cross-sectional view of the carrier member and the drug-delivery sleeve of FIG. 5A through a line A-A of FIG. 5A, in accordance with embodiments of the present invention;

FIG. 7A is a side perspective view of a drug-delivery tip attachment attached to a carrier member, in accordance with embodiments of the present invention;

FIG. 7B is a cross-sectional view of the electrode assembly and the tip attachment of FIG. 7A, in accordance with embodiments of the present invention;

FIG. 7C is a cross-sectional view of the electrode assembly and the tip attachment of FIG. 7A along a line A-A of FIG. 7A, in accordance with embodiments of the present invention;

FIG. 8A is a side perspective view of a drug-delivery tip attachment attached to a carrier member, in accordance with embodiments of the present invention; and FIG. 8B is a cross-sectional view of the electrode assembly and the tip attachment of FIG. 8A, in accordance with embodiments of the present invention.

DETAILED DESCRIPTION

Figure 1A:
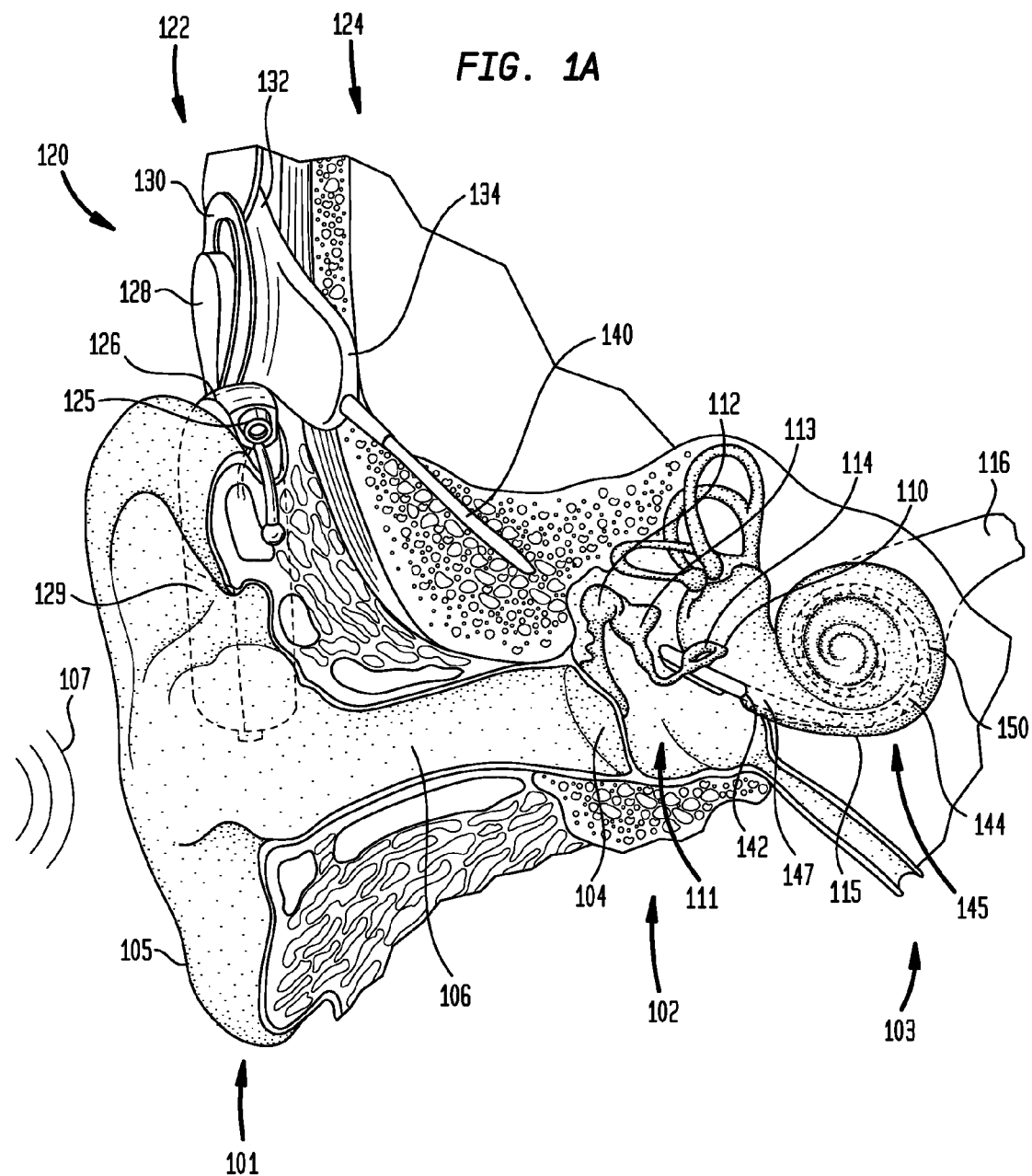
FIG. 1A is a perspective view of an exemplary cochlear implant with which a drug-delivery accessory of the present invention may be implemented.

The present invention is directed to a drug-delivery accessory for an implantable medical device having one or more components. Embodiments of the drug-delivery accessory include drug-delivery sleeves and drug-delivery tip attachments releasably carrying (e.g., covered with, impregnated with, etc.) one or more drugs. Aspects of the present invention are directed to a drug-delivery accessory for an implantable elongate carrier member, lead, catheter or the like (collectively and generally referred to as a "carrier member") of an implantable medical device.

Embodiments of the drug-delivery accessory are physically separate from the implantable medical device having one or more implantable components. As such, the drug-delivery accessory may be manufactured separately from the device components, which is referred to herein as being "separate" from the medical device. The drug-delivery accessory is operationally combined with a component of the implantable medical device subsequent to the device's manufacture and/or sterilization. Embodiments of the drug-delivery accessory may be configured, for example, to attain an implanted position adjacent to one or more surfaces of an implantable medical device component. In certain embodiments, the accessory is configured in the form of a sleeve, collar, ring, band, or the like (collectively and generally referred to as a "sleeve" herein), to receive and to partially or completely wrap around or envelop all or a portion of one or more components of an implantable medical device. In other embodiments, the accessory is configured in the form of a tip attached to, mounted to and/or fixed on the distal tip of an implantable elongate component of an implantable medical device. Embodiments of the drug delivery accessory may be implanted into the recipient concurrently with, to the implantation of the implantable medical device. As used herein, the term "implantable medical device" encompasses both partially implantable and fully implantable medical devices.

Providing an independently-manufactured and physically distinct drug-delivery accessory to an implantable medical device increases flexibility in an applied therapy while reducing the undesirable aspects associated with manufacturing an implantable medical device with a drug integrated therein.

At least some conventional medical device manufacturing processes include applying a drug to a component of the medical device. In one example, a drug is applied to a cochlear implant during the manufacturing process for the cochlear implant. In some conventional applications, a drug carried by the cochlear implant may be released via elution or through resorption of a feature carrying the drug. In these applications, the elution and the resorption are each triggered by interaction with moisture. In an intra-cochlear environment, the triggering moisture is perilymph fluid present in the cochlea. However, the medical device may also be exposed to moisture (e.g., ethanol, lenium, deionized water, a soap solution, and n-Heptane) during the manufacturing process. Such exposure may initiate the elution of the drug or the dissolution of a resorbable feature carrying the drug, which may leave the medical device carrying an unknown quantity of the drug at the end of the manufacturing process. Additionally, the elution profile of a drug carried by the medical device may be affected at temperatures greater than 150° C., which can be problematic, as temperatures experienced during the manufacture of a cochlear implant, for example, can be greater than 100° C. However, re-designing a cochlear implant manufacturing process to accommodate a drug-delivery feature is not practical or cost-effective.

Embodiments of the present invention provide an independently-manufactured and physically distinct drug-delivery accessory for an implantable medical device. As such, the drug delivery accessory can be applied to the medical device after the manufacturing process (e.g., at the time of surgery), which enables the drug-delivery accessory to be more consistent and reliable. This also enables manufacturing efforts to be focused solely on the successful manufacture of the implantable medical device rather than on manufacturing an integrated assembly of the device and a drug-delivery mechanism.

Additionally, providing an independently-manufactured and physically distinct drug-delivery accessory to an implantable medical device also increases flexibility in an applied therapy. For example, as described in more detail below, the type, location and/or dosage of a drug applied to a recipient may all be selected after manufacture (e.g., at the time of surgery). Also, in some embodiments of the present invention, an implantable medical device may be manufactured as a universal device that may be complemented with different embodiments of the drug-delivery accessory. This advantageously enables a single implantable component to be manufactured and inventoried for a length of time not determined by a drug. This is particularly advantageous in those circumstances in which the drug to be delivered via the accessory has a limited shelf life.

As used herein, the term "drug" refers to any bioactive substance now or later developed, including, but not limited to, pharmaceuticals and other chemical compounds such as those intended to provide therapeutic benefits to, or other reactions in, an implant recipient, whether localized or distributed throughout the recipient. Such bioactive substances may include, for example, steroids or other anti-inflammatory drugs to reduce inflammation at the implantation site. Another class of bioactive substances that may be included in the drug-delivery accessories are antibiotics to mitigate bacterial growth related to the implantation of the medical device.

Embodiments of the invention are not necessarily drawn to scale in the accompanying drawings. Rather, the dimensions of elements shown in the drawings are exaggerated for illustrative purposes.

FIG. 1A is a perspective view of an exemplary cochlear implant with which a drug-delivery accessory of the present invention may be implemented. In fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104, which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound. In deaf persons, there is an absence or destruction of the hair cells. A cochlear implant 120 is utilized to stimulate directly the ganglion cells to provide a hearing sensation to the recipient.

FIG. 1A also shows the positioning of cochlear implant 120 relative to outer ear 101, middle ear 102 and inner ear 103. Cochlear implant 120 comprises external component assembly 122, which is directly or indirectly attached to the body of the recipient, and an internal component assembly 124 which is temporarily or permanently implanted in the recipient. External assembly 122 comprises microphone 125 for detecting sound that is outputted to a behind-the-ear (BTE) speech processing unit 126 that generates coded signals which are provided to an external transmitter unit 128, along with power from a power source 129 such as a battery. External transmitter unit 128 comprises an external coil 130 and, preferably, a magnet (not shown) secured directly or indirectly in external coil 130.

Internal component assembly 124 comprise an internal coil housing 132 that receives and transmits power and coded signals received from external assembly 122 to a stimulator unit 134 to apply the coded signal to cochlea 115 via an implanted electrode assembly 140. An intra-cochlear region 145 of electrode assembly 140 enters cochlea 115 at cochleostomy region 142 and has one or more electrodes 150 positioned on an electrode array 144 so as to be substantially aligned with portions of tonotopically-mapped cochlea 115. Signals generated by stimulator unit 134 are typically applied by an array 144 of electrodes 150 to cochlea 115, thereby stimulating auditory nerve 116. Additionally, intra-cochlear region 145 of electrode assembly 140 has a proximal end 147 disposed near cochleostomy region 142 when intra-cochlear region 145 is implanted in cochlea 115.

Given the coiling shape of cochlea 115, cochlear implant devices such as electrode assembly 140 are often constructed using a material, or combination of materials, which curls or is capable of being curled in a manner which follows the curvature of cochlea 115. The portion of electrode assembly 140 intended to be inserted into cochlea 115 will often have a stiffening stylet (not shown) inserted into a channel, for example a lumen (not shown), which extends distally from the proximate end of electrode assembly 140. During implantation of electrode assembly 140, the stylet contained in the lumen of electrode assembly 140 is removed from the proximate end of electrode assembly 140 as electrode assembly 140 is inserted into cochlea 115. The act of removing the stiffening stylet from the lumen allows electrode assembly 140 to curl. In further embodiments of cochlear implant 120, the stiffness of the stylet decreases in response to fluids and/or body temperature allowing electrode assembly 140 to curl in order to follow the curvature of the inner walls of cochlea 115. In other embodiments of cochlear devices, electrode assembly 140 is naturally straight without the assistance of a stylet inserted into the lumen. Electrode assembly 140 is constructed using a flexible material, or is constructed so as to flex upon a fixed amount of force being exerted on the tip or body of electrode assembly 140 as it is being inserted into cochlea 115. In other embodiments, electrode assembly 140 has a length that results in it extending to the first turn of cochlea 115. In further embodiments of implanted cochlear devices, the stylet becomes flexible in response to fluids and/or body temperature thereby allowing electrode assembly 140 to curl so as to follow the curvature of the inner wall of cochlea 115.

As one of ordinary skill in the art will appreciate from the present disclosure, embodiments of the present invention may be advantageously implemented in a variety of implantable medical devices, components, etc. ("devices" herein). Although cochlear implant 120 described above with reference to FIG. 1A is a partially-implantable device, embodiments of the present invention also provide benefits to devices that have limited sources of power such as fully-implantable prosthetic hearing devices including fully-implantable bone-anchored hearing aids, fully-implantable cochlear implants, middle ear implants, and the like. Embodiments of the present invention may also provide benefits to other types of implantable medical devices that have various types of elongate components, such as leads or catheters.

Figure 1B:
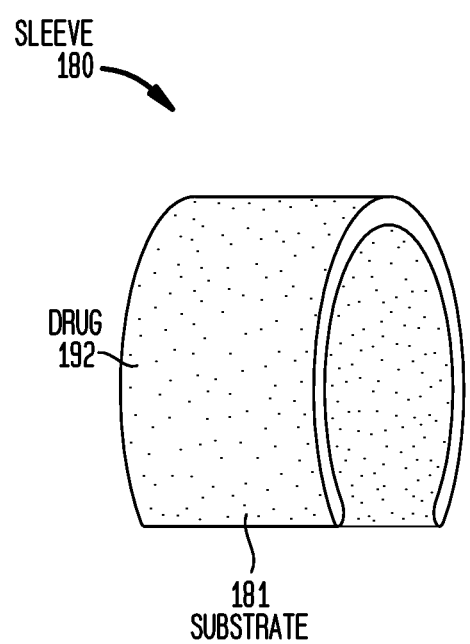
FIG. 1B is a side view of a region or portion of an exemplary drug-delivery accessory, in accordance with embodiments of the present invention.

FIG. 1B is a side view of a region or portion of an exemplary drug-delivery accessory, in accordance with embodiments of the present invention. Specifically, the drug-delivery accessory shown in FIG. 1B is a drug-delivery sleeve 180 that comprises a substrate (or body) 181. A drug 192 is releasably carried in or on (collectively and generally "in" herein) substrate 181 of sleeve 180. That is, a drug 192 is releasably secured in substrate 181 such that drug 192 is implanted in the recipient with sleeve 280 so as to complement an implantable device or component (not shown in FIG. 1B). The drug 192 is subsequently released in to the body of the recipient in which the sleeve 180 and its complementary component are implanted. In certain embodiments, the drug 192 carried by substrate 181 may be released via elution or through resorption of substrate 181. In other embodiments, drug 192 can be dispersed in an ionic fluid or solution that is allowed to diffuse or migrate and/or is expelled from pores in substrate 181 under application of a suitable electric field. In such embodiments, substrate 181 may be constructed of a porous metallic material, such as porous platinum.

For ease of illustration, components of drug 192 are schematically illustrated as small dots distributed across substrate 181. It should be appreciated, however, that the quantity of different drugs, the amount of each such drug, the location of such drug or drugs, and so on, may be determined based on the particular substrate 181, drug or drugs 192, the condition or conditions to be treated by the drug or drugs, the implant location, recipient physiology and other factors.

Substrate 181 may be composed of a variety of materials, and have a variety of structures, depending on the particular application and type of drug(s) 192 which substrate 181 is to carry. It should also be appreciated that the mechanism by which drug 192 is releasably secured in substrate 181 of drug-delivery sleeve 180 may be a characteristic of substrate 181, a characteristic of drug 192, or a characteristic of both substrate 181 and drug 192. Additionally or alternatively, an additional treatment or agent may be employed to releasably secure drug 192 in substrate 181. While a drug-delivery accessory has been described above in relation to an exemplary drug-delivery sleeve 180, drug-delivery accessories in accordance with embodiments of the invention are not limited to sleeves. For example, as described further below, a drug-delivery accessory in accordance with embodiments of the present invention may be a drug-delivery tip attachment.

As discussed elsewhere herein, a drug-delivery accessory in accordance with embodiments of the present invention may be used to complement a number of different implantable components of a variety of implantable medical devices. For example, referring specifically to cochlear implants, a drug-delivery accessory in accordance embodiments of the present invention may complement an electrode assembly, such as the electrode assembly 140 of FIG. 1A. For ease of illustration, embodiments of the present invention will be described with reference to a drug-delivery sleeve or tip attachment used in conjunction with an electrode assembly of a cochlear implant. Such examples are merely illustrative and should not be construed as limiting the present invention. Embodiments of the present invention may also provide benefits to other types of implantable medical devices, and particularly those having any one of various types of implantable elongate components, such as leads or catheters.

It may be desirable for embodiments of the drug-delivery accessory of the present invention to be constructed of a material that is resorbable, bio-resorbable, bio-degradable, and/or dissolvable (generally and collectively referred to herein as "resorbable"), so that while bioactive substances are being absorbed at the implant site, or after they are absorbed, the drug-delivery accessory may be partially or completely resorbed by the tissue surrounding the implant site. In certain embodiments, the drug-delivery accessory is comprised of a resorbable material that partially or completely degrades over time through interaction with various body fluids. In other embodiments, the drug-delivery accessory is comprised of a resorbable material that partially or completely degrades over time through exposure to body temperatures and/or fluids. Alternatively, the drug-delivery accessory may be comprised of a resorbable material that partially or completely degrades in response to an external catalyst (i.e., a catalyst that is not a substance normally present or a condition normally occurring in a recipient's body).

However, it may also be desirable for the drug-delivery accessory to be constructed of a non-resorbable material. The use of a non-resorbable material may offer different benefits from the use of a resorbable material, such as the continued provision of spacing or support for other tissue or implanted components. For example, the drug-delivery accessory may be made of a polymeric material configured to enable bioactive substances to be embedded within the structure of the polymeric material, and to release the bioactive substances either naturally or through the interaction of body fluids or body heat that may permeate the accessory.

Embodiments of the drug-delivery accessory of the present invention may be manufactured by molding the accessory from a substance that has been combined with one or more drugs. In certain embodiments, prior to molding, a curable substance in an uncured state is combined with one or more drugs to form a molding mixture. In certain embodiments, the curable substance may be a silicone in its uncured state (e.g., LSR 30). An assembly is then placed into a molding die and injected with the molding mixture containing the one or more drugs. The mixture is then cured by a means suitable for the curable substance used. For example, when room-temperature vulcanization (RTV) silicone is the curable substance, the silicone may be exposed to the appropriate environmental conditions and allowed to cure. Alternatively, when using platinum-cured silicone it may be cured through appropriate heating, and when ultra-violet (UV) cured silicone is used it may be cured through exposure to UV light. Subsequently, the completed drug-delivery accessory may be removed from the die.

Figure 2A:
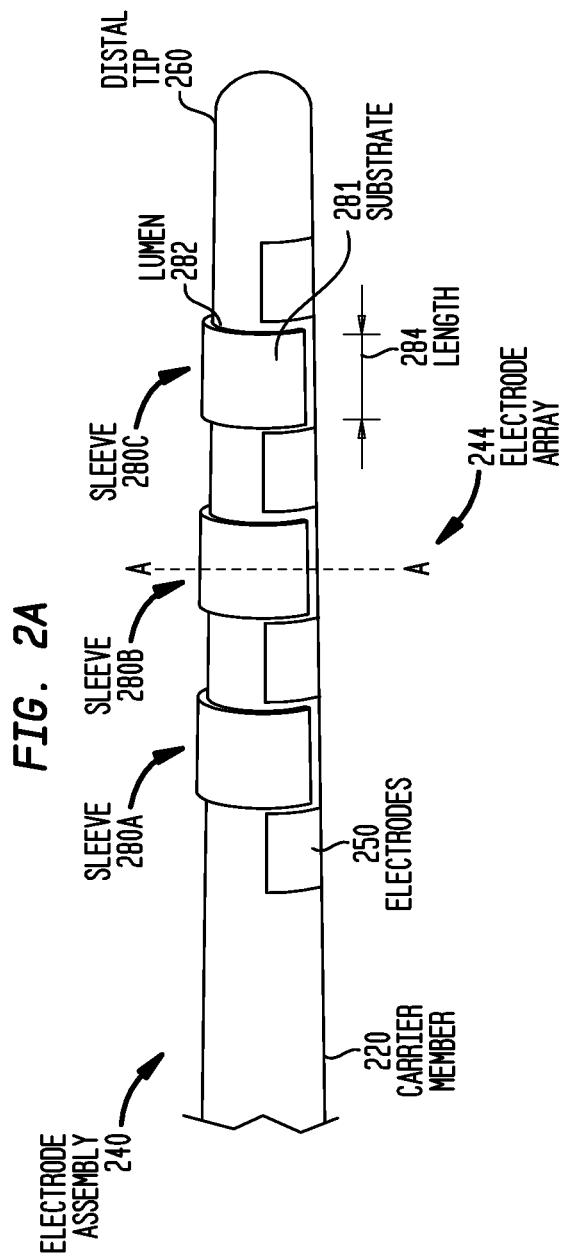
FIG. 2A is a side perspective view of a plurality of drug-delivery sleeves disposed on a carrier member, in accordance with embodiments of the present invention.

FIG. 2A is a side perspective view of a plurality of drug-delivery sleeves 280 disposed on a carrier member 220, in accordance with embodiments of the present invention. In the illustrative embodiment of FIG. 2A, three drug-delivery sleeves 280 are illustrated (i.e., sleeves 280A, 280B and 280C). However, in embodiments of the present invention, any number of drug-delivery sleeves 280 may be disposed on carrier member 220.

As illustrated in FIG. 2A, electrode assembly 240, which is an embodiment of electrode assembly 140 of FIG. 1A, comprises a carrier member 220 having an electrode array 244. Electrode array 244 includes a plurality of electrodes 250 longitudinally spaced along carrier member 220. Prior to inserting electrode assembly 240 into a cochlea of a recipient, one or more drug-delivery sleeves 280 may be positioned on carrier member 220. Each drug-delivery sleeve 280 comprises a tubular substrate 281, and a lumen 282 having a diameter 285 and configured to receive a portion of carrier member 220. In certain embodiments, a drug-delivery sleeve 280 may be placed over distal tip 260 of carrier member 220 and then longitudinally displaced (e.g., moved or slid) along carrier member 220 until drug-delivery sleeve 280 reaches a desired location on carrier member 220. Alternatively, leading with distal tip 260, carrier member 220 may be threaded through lumen 282 until sleeve 280 reaches a desired location on carrier member 220.

Figure 2B:
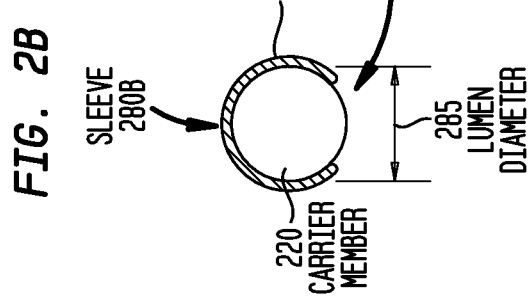
FIG. 2B is a cross-sectional view of the carrier member and one of the sleeves of FIG. 2A through a line A-A of FIG. 2A, in accordance with embodiments of the present invention.

FIG. 2B is a cross-sectional view of carrier member 220 and sleeve 280B through line A-A of FIG. 2A. As illustrated in FIG. 2B, sleeve 280B has a substantially C-shaped cross-section and is configured to substantially surround a circumference of carrier member 220. Sleeve 280B includes a gap 283 and as such does not completely surround a circumference of carrier member 220. In alternative embodiments, each of sleeves 280 may have a substantially U-shaped cross-section and be configured to at least partially surround a circumference of carrier member 220. A sleeve 280 with a U-shaped cross-section may have a larger gap than gap 283 illustrated in FIG. 2B. In other embodiments, each of sleeves 280 may have a substantially circular cross-section and be configured to completely surround a circumference of carrier member 220 (see, e.g., FIGS. 3A and 3B).

In the illustrative embodiment of FIG. 2A, carrier member 220 tapers toward distal tip 260. That is, carrier member 220 tapers distally. As used herein, an element "tapers distally" when it tapers toward a distal end or tip of the element. Each sleeve 280 of FIG. 2A has a lumen 282 with a diameter 285 that is large enough to allow distal tip 260 to pass through lumen 282. After distal tip 260 passes through lumen 282 of a sleeve 280, the sleeve 280 may be displaced along carrier member 220 away from distal tip 260. The sleeve 280 then passes over progressively wider portions of carrier member 220 until the sleeve 280 reaches a position along carrier member 220 at which the diameter of carrier member 220 is greater than or equal to the diameter 285 of lumen 282. At that position, carrier member 200 will prevent further movement of the sleeve 280 away from distal tip 260. A sleeve 280 may be secured to or otherwise retained stationary on carrier member 220 at or near the position at which the diameter of carrier member 220 is greater than or equal to the diameter 285 of lumen 282. In certain embodiments, sleeve 280 may be retained stationary at or near this location via an interference or friction fit.

FIG. 2A illustrates a plurality of differently-sized drug-delivery sleeves positioned along carrier member 220. The respective lumens 282 of sleeves 280A, 280B and 280C each have a different diameter 285. As such, each of sleeves 280 is configured to advance to a different position along carrier member 220. In the illustrative embodiment of FIG. 2A, sleeve 280A has the lumen 282 with the greatest diameter 285, and sleeve 280A is configured to advance the farthest along carrier member 220 away from distal tip 260. Sleeve 280B has a lumen 822 with a smaller diameter 285 and will not advance as far as sleeve 280A. Sleeve 280C has the lumen 282 with the smallest diameter 285 and will not advance as far as sleeve 280B. In other embodiments, sleeves 280 are malleable, and each of sleeves 280 may be secured to or otherwise retained stationary on carrier member 220 by clamping or compressing the sleeve 280 to carrier member 220 once the sleeve 280 has been located at a desired position along carrier member 220. In certain embodiments, sleeve 280 may be clamped or compressed to carrier member 220 manually using a force approximately equal a force that may be applied by hand.

In the illustrative embodiment of FIG. 2A, each of drug-delivery sleeves 280 is a drug-delivery ring. As used herein, a "drug-delivery ring" or "ring" is a drug-delivery sleeve having a length that is smaller than a distance between adjacent electrodes of a carrier member configured to receive the sleeve. As illustrated in FIG. 2A, each of drug-delivery sleeves 280 has a length 284 that is smaller than the distance between adjacent electrodes 250 of carrier member 220 and may be positioned between adjacent electrodes 250. Because drug-delivery sleeves 280 may be positioned between adjacent electrodes 250, sleeves 280 may be constructed of a non-resorbable material. Non-resorbable sleeves 280 will remain on carrier member 220 after implantation and the release of drug(s) carried by sleeves 280. However, when properly positioned between electrodes 250, such non-resorbable sleeves 280 will not effect stimulation by covering any of electrodes 250.

In alternative embodiments, drug-delivery sleeves 280 may be constructed of a resorbable material. For example, substrates 281 of sleeves 280 may be constructed of a resorbable material. In such embodiments, if drug-delivery sleeves 280 are placed over one or more electrodes 250, the sleeves 280 will not effect stimulation by electrodes 250 once sleeves 280 are completely resorbed. Another advantage of completely resorbable sleeves 280 is that the sleeves 280 will not remain in the cochlea indefinitely. By contrast, a sleeve 280 having a substrate 281 fabricated from silicone, for example, would remain in the cochlea after releasing drug(s). By remaining in the cochlea, sleeve 280 could create a location for harmful microbes to gather since sleeve 280 is separate from carrier member 220. In certain embodiments, resorbable drug-delivery sleeves are constructed of one or more biodegradable polymers. Examples of suitable biodegradable polymers include poly(acrylic acid), poly(ethylene glycol), poly(vinylpyrrolidone), poly(hydroxybutyrate), poly(lactide-co-glycolide), and polyanhydrides.

Drug-delivery sleeves described herein in accordance with embodiments of the present invention may be manufactured separately from, for example, a carrier member of an implantable medical device, and may be positioned on the carrier member subsequent to the carrier member's manufacture or sterilization. Providing independently-manufactured and physically distinct (i.e., "separate") drug-delivery sleeves in accordance with embodiments of the present invention increases flexibility for the application of therapy. In certain embodiments, separate drug-delivery sleeves releasably carrying different types of drugs are provided, allowing the type of drug to be applied to be selected after manufacture of the implantable device, such as at the time of surgery. Accordingly, when the electrode assembly is to be inserted through a cochleostomy, for example, a drug that encourages fibrous tissue growth to achieve a faster and stronger cochleostomy seal may be selected. Alternatively, when the electrode assembly is to be inserted through the round window, a drug that encourages sealing of the round widow may be selected. This drug may be different from the drug that encourages fibrous tissue growth since no new bone growth is necessary after inserting an electrode assembly through the round window. In addition, multiple drug-delivery sleeves releasably carrying different drugs may be selected so that multiple different drugs can be applied to a recipient simultaneously.

In certain embodiments of the present invention, separate drug-delivery sleeves having different dosages may be provided, allowing the dosage of the drug(s) to be selected after manufacture of the implantable device. For example, drug-delivery sleeves releasably carrying different amounts of a drug may be provided. Additionally or alternatively, the dosage of the drug(s) may be selected by choosing the number of drug-delivery sleeves to position on the carrier member. For example, a relatively large number of drug-delivery sleeves may be positioned on the carrier member to apply a relatively large dose of a drug, and a relatively small number of drug-delivery sleeves may be positioned on the carrier member to apply a relatively small dose of a drug.

Providing separate drug-delivery sleeves also allows the location at which a drug is to be applied within a recipient to be chosen after manufacture of the carrier member, such as at the time of surgery. A location in a recipient may be targeted for drug delivery by choosing one or more drug-delivery sleeves having the appropriate size(s). A chosen location within a recipient may be targeted by positioning a drug-delivery sleeve 280 on a portion of carrier member 220 configured to be adjacent to the chosen location when implanted. As noted above, drug-delivery sleeves 280 having different lumen widths are configured to advance to different positions along tapered carrier member 220. As such, a location in a recipient may be targeted by selecting a drug-delivery sleeve 280 having an appropriate lumen width.

In certain embodiments, the location chosen for application of the drug may be a location that is advantageous for the release of the drug. One such location is adjacent to the cochlear aqueduct. The cochlear aqueduct is connected to a port in the cochlea, and there is therefore more movement of cochlear fluid (e.g., back-and-forth movement) adjacent to the cochlear aqueduct than in other places of the cochlea. Accordingly, better drug release may be achieved by selecting one or more drug-delivery sleeves such that, when inserted with the carrier member, the drug-delivery sleeve(s) are located adjacent to the cochlear aqueduct. Another location that may be advantageous for the release of the drug is a location adjacent to the stapes footplate. In many cochlear implant recipients, the stapes footplate still moves, creating pressure waves within the cochlea. Thus, drugs may travel well from a location in the cochlea that is adjacent to the stapes footplate.

Additionally, various combinations of the type, location and/or dosage of one or more drugs may be selected in accordance with embodiments of the present invention. Certain embodiments of the present invention allow for different types of drugs to be applied to different locations within a recipient, which can be beneficial in the context of a cochlear implant, for example.

In one specific example, referring to FIG. 1A, after implanting electrode assembly 140 into cochlea 115 through cochleostomy region 142, sealing the tissue at cochleostomy region 142 is important so that cochleostomy region 142 does not become a pathway for pathogens. Additionally, it has been theorized that a delay in forming a cochleostomy seal can reduce residual hearing. As such, it is desirable to apply a drug, such as ciprofloxacin, which encourages rapid and strong formation of a cochleostomy seal at or near cochleostomy region 142. However, application of this type of drug is not as desirable in more apical regions of the cochlea, where fibrous tissue growth impedes stimulation. Rather, the preferred drug would maintain the spiral ganglion cells. Also, in recipients with residual hearing, the residual hearing is typically in a low frequency range. As such, for these recipients, a preferred drug would preserve function in the region of the cochlea mapped to that low frequency range, and in a region of the cochlea mapped to a high frequency range, the preferred drug would maintain the spiral ganglion cells. Accordingly, an anti-inflammatory drug, such as dexamethasone, may be beneficial in more apical regions of the cochlea. Such an anti-inflammatory drug may assist in preserving residual hearing in regions of the cochlea mapped to relatively low frequencies, and assist in maintaining the spiral ganglion cell in regions of the cochlea mapped to relatively high frequencies. However, the anti-inflammatory drug must be kept a sufficient distance away from the cochleostomy site (preferably no closer than 3.5 mm from the cochleostomy site) so that the drug will not interfere with the healing of an insertion site (e.g., a cochleostomy or the round window).

In certain embodiments of the present invention, a first type of drug may be selected for application at a first location, and a second type of drug may be selected for application at a second location. For example, one or more sleeves 280 carrying Ciprofloxacin and having lumen widths allowing them to be positioned near a proximal end (see 147 of FIG. 1A) of the carrier member may be positioned on carrier member 220 prior to insertion, and one or more sleeves 280 carrying dexamethasone and having lumen widths allowing them to be positioned near a distal end of the carrier member may be positioned on carrier member 220 prior to insertion. As such, sleeves 280 may be selected such that, after implantation of carrier member 220, one or more sleeves 280 carrying ciprofloxacin are located adjacent to cochleostomy region 142 and one or more sleeves 280 carrying dexamethasone are located in more apical regions of the cochlea. Additionally, using lumen widths as a guide, for example, sleeves 280 carrying dexamethasone may be selected such that they will be no closer than 3.5 mm from the cochleostomy site upon insertion of carrier member 220.

FIG. 3A is a side perspective view of a drug-delivery sleeve 387 disposed on a carrier member 220, in accordance with embodiments of the present invention. In the illustrative embodiment of FIG. 3A, multi-ring drug-delivery sleeve 387 comprises a plurality of drug-delivery rings 380 connected by an attachment frame 375. As shown in FIG. 3A, rings 380 are unitary with frame 375. Rings 380 are similar to sleeves 280 of FIGS. 2A and 2B. Each of rings 380 comprises a tubular substrate 381 and a lumen 382. However, unlike sleeves 280 illustrated in FIGS. 2A and 2B, each of drug-delivery rings 380 has a substantially circular cross-section, as shown in FIGS. 3A and 3B. None of rings 380 includes a gap analogous to gap 283 of sleeves 280. Instead, in the embodiment illustrated in FIGS. 3A-3B, each of rings 380 completely surrounds a circumference of carrier member 220. In the illustrative embodiment of FIG. 3A, attachment frame 375 has a length 384 extending between first and second ends of multi-ring drug-delivery sleeve 387. As shown, rings 380 are aligned along length 384 of attachment frame 375 such that carrier member 220 is positionable in the respective lumens 382 of each of rings 380 concurrently.

FIG. 3B is a cross-sectional view of carrier member 220 and a drug-delivery ring 380 through line A-A of FIG. 3A. As illustrated in FIG. 3B, ring 380 has a lumen diameter 835 and a substantially circular cross-section, and is configured to completely surround a circumference of carrier member 220. In alternative embodiments, one or more of rings 380 may be configured to at least partially surround a circumference of carrier member 220 with a substantially C-shaped or a substantially U-shaped cross-section including a gap similar to gap 283 of sleeves 280 (see, e.g., FIGS. 2A and 2B).

While multi-ring drug-delivery sleeve 387 of FIG. 3A comprises four drug-delivery rings 380, in alternative embodiments, sleeve 387 may comprise any number of rings 380. In certain embodiments, sleeve 387 may extend from a location adjacent distal tip 260 to a location adjacent a proximal end (see 147 of FIG. 1A) of carrier member 220 that is configured to be implanted adjacent to a cochleostomy. In such embodiments, sleeve 387 may comprise a relatively large number of rings 380 spaced at intervals approximately equal to the lengths of electrodes 250. In other embodiments, rings 380 may be spaced at larger or smaller intervals.

Alternatively, rings 380 may be spaced at uneven intervals and/or in various groupings along attachment frame 375. For example, multi-ring drug-delivery sleeve 387 may comprise a first plurality of rings 380 at a proximal end of sleeve 387 and a second plurality of rings 380 at a distal end of sleeve 387 and spaced apart from the first plurality. In such an embodiment, sleeve 387 may be configured such that the first plurality rings 380 can be positioned near the proximal end of carrier member 220, and the second plurality of rings 380 can be positioned near the distal end of carrier member 220. In other embodiments, similar to sleeves 280 of FIGS. 2A and 2B, a plurality of sleeves 387 configured to advance to different positions along carrier member 220 may be provided.

In certain embodiments, attachment frame 375 is severable so that one or more rings 380 may be detached from the remainder of multi-ring drug-delivery sleeve 387 and positioned on carrier member 220 separately from the remainder of sleeve 387. In such embodiments, attachment frame 375 may comprise a plurality of severable regions 330 at which attachment frame 375 may be readily severed. In the embodiment illustrated in FIG. 3A, severable regions 330 each comprise a plurality of openings 332 around a circumference of multi-ring sleeve 387 separated by relatively small portions of attachment frame 375 remaining between openings 332. The openings 332 of a severable region 330 may allow frame 375 to be readily cut or torn at the severable region 330. Alternatively, a severable regions may include a thinned region at which less material is present allowing attachment frame 375 to be readily cut or torn. In alternative embodiments, the physical characteristics of frame 375 are no different at severable regions 330 than at other regions of frame 375. For example, severable regions 330 may not include any openings or thinned regions, but may still serve as regions at which portions of sleeve 387 may be severed from one another. In such embodiments, frame 375 may still be cut or torn at severable region 330; however, frame 375 may not be cut or torn as readily as in embodiments including openings or thinned regions, for example. Frame 375 may be cut using a suitable cutting tool. Additionally, in certain embodiments, attachment frame 375 may releasably carry one or more drugs, like rings 380. In other embodiments, attachment frame 375 does not releasably carry any drug. Also, in accordance with embodiments of the present invention, attachment frame 375 may be resorbable or non-resorbable.

The configuration of multi-ring drug-delivery sleeve 387, in accordance with embodiments of the present invention, may assist a surgeon, for example, in selecting the appropriate ring(s) 380 for a desired therapy. For example, if the surgeon desires to apply therapy only adjacent to several of the most distal electrodes 250, the surgeon may sever a subset of rings 380 from the distal end of sleeve 387 at one of the severable regions 330, and position the subset on carrier member 220 after manufacture of the electrode assembly 240 but prior to implantation.

FIG. 4A is a side perspective view of a drug-delivery sleeve 480 disposed on a carrier member 220, in accordance with embodiments of the present invention. Drug-delivery sleeve 480 comprises a tubular substrate 481 and a lumen 482 configured to receive a portion of carrier member 220. In certain embodiments, drug-delivery sleeve 480 may be placed over distal tip 260 of carrier member 220 and then longitudinally displaced along carrier member 220 until drug-delivery sleeve 480 reaches a desired location on carrier member 220. Alternatively, leading with distal tip 260, carrier member 220 may be threaded through lumen 482 until sleeve 480 reaches a desired location on carrier member 220.

FIG. 4B is a cross-sectional view of carrier member 220 and sleeve 480 through line A-A of FIG. 4A. As illustrated in FIG. 4B, sleeve 480 has a substantially C-shaped cross-section and is configured to substantially surround a circumference of carrier member 220. Sleeve 480 includes a gap 483 and as such does not completely surround a circumference of carrier member 220. Alternatively, sleeve 480 may have a substantially U-shaped cross-section and be configured to at least partially surround a circumference of carrier member 220. A sleeve 480 with a U-shaped cross-section may have a larger gap than gap 483 illustrated in FIG. 4B. In other embodiments, sleeve 480 may have a substantially circular cross-section and be configured to completely surround a circumference of carrier member 220 (see, e.g., FIGS. 5A and 5B).

Similar to sleeves 280 of FIG. 2, in the illustrative embodiment of FIGS. 4A and 4B, sleeve 480 has a lumen 482 with a diameter 485 that is large enough to allow distal tip 260 to pass through lumen 485. In the illustrative embodiment of FIGS. 4A and 4B, the diameter 485 of lumen 482 varies along the length 484 of sleeve 480. In such embodiments, lumen 482 has multiple different diameters along the length 484 of sleeve 480. Lumen diameter 485 illustrated in FIG. 4B is the diameter 485 of lumen 482 at line A-A of FIG. 4A. In alternative embodiments, the diameter 485 of lumen 482 is constant along the length 484 of sleeve 480.

After distal tip 260 passes through lumen 482 of sleeve 480, sleeve 480 may be displaced along carrier member 220 away from distal tip 260. Sleeve 480 then passes over progressively wider portions of carrier member 220 until sleeve 480 is positioned such that a portion of lumen 482 having a first diameter 485 is positioned at least partially around a portion of carrier member 220 having a diameter that is greater than or equal to the first diameter 485. At that position, carrier member 220 will prevent further movement of sleeve 480 away from distal tip 260. In certain embodiments, sleeve 480 is secured to or otherwise retained stationary at or near that position of carrier member 220 via a friction or interference fit. In certain embodiments, sleeve 480 may be positioned such that multiple portions of lumen 482 having multiple diameters 485 are respectively positioned at least partially around portions of carrier member 220 having diameters that are greater than or equal to the respective diameters 485. In some embodiments, sleeve 480 may also be secured to or otherwise retained stationary on carrier member 220 as described above in relation to sleeves 280 of FIG. 2.

The length 484 of drug-delivery sleeve 480 is much greater than the length 284 of each of rings 280 of FIG. 2A. In the illustrative embodiment of FIG. 4A, the length 484 of drug-delivery sleeve 480 is large enough that drug-delivery sleeve 480 at least partially covers multiple electrodes 250 at once. The length 484 of drug-delivery sleeve 480 illustrated in FIG. 4A is merely exemplary. In embodiments of the present invention, sleeve 480 may have a length that is as small as that of a ring 280, or a length long enough for sleeve 480 to extend from distal tip 260 to a proximal end (see 147 of FIG. 1A) of carrier member 220 that is disposed near a cochleostomy when carrier member 220 is implanted.

In certain embodiments, drug-delivery sleeve 480 is constructed of a resorbable material that completely degrades over time through interaction with one or more of various body fluids, through exposure to body temperatures, and/or through interaction with or exposure to any other substance or condition present within a recipient's body. Sleeve 480 may be positioned at least partially over one or more electrodes 250 prior to implantation of carrier member 220. Because drug-delivery sleeve 480 is resorbable, stimulation will not be effected once sleeve 480 is resorbed. However, sleeve 480 may effect the stimulation provided by any electrodes 250 that it covers until sleeve 480 is resorbed.

In certain embodiments of the present invention, it is desirable to achieve a sustained drug release over a period of up to ninety days. In some embodiments, a resorbable sleeve will have an initial release of the drug upon implantation, followed by a second phase of additional drug release that is sustained over a longer period of time. Additionally, the longer the sustained drug release period lasts (for example, up to a maximum of ninety days), the more benefit a recipient will receive from the drug release. However, as noted above, sleeve 480 will effect the stimulation provided by any electrodes 250 that it covers until it is resorbed. Accordingly, in certain embodiments, steps may be taken to account for the effect of sleeve 480 on the electrodes 250 that it covers before complete resorption of sleeve 480. For example, in some embodiments, the characteristics of stimulation provided by an electrode 250 covered by a sleeve 480 may be determined so that they may be accounted for in the programming of the cochlear implant.

A cochlear implant converts external stimuli in the form of acoustic sound into a sequence of electrical stimuli that are applied to electrodes implanted within the cochlea. To perform this task, there are a large quantity of parameters that are involved in the configuration of a cochlear implant. The configuration of a cochlear implant is commonly referred to as a "fitting" and the parameters are commonly referred to as MAP parameters. Varying the values of the MAP parameters in turn alters the processing characteristics of the cochlear implant as it converts acoustic sound information to associated electrical stimuli. Additionally, cochlear implant fitting involves the configuration of the MAP parameters that affect the stimulation pattern and sound processing of the cochlear implant.

By covering one or more electrodes 250, sleeve 480 will effect the patient's MAP. In addition, sleeve 480 will effect the stimulation provided by an electrode 250 differently over time as sleeve 480 progressively degrades (e.g., becomes smaller and/or thinner). Thus, in certain embodiments, a recipient's MAP may be changed over time as sleeve 480 is progressively resorbed over time. For example, a cochlear implant recipient may have the MAP changed via frequent re-fitting sessions performed by an audiologist during time period in which sleeve 480 is still being resorbed. Alternatively, in some embodiments of the invention, a cochlear implant may be provided with an auto-fitting function by which a recipient may perform a fitting process to adjust his or her MAP without the assistance of an audiologist. This auto-fitting function may be performed daily, for example, in order to account for the changes in sleeve 480 as it degrades over time.

Alternatively, in certain embodiments of the present invention, sleeve 480 may be conductive in order to mitigate the effect of sleeve 480 on stimulation. For example, a conductive sleeve 480 (e.g., substrate 481) may be formed from polyvinyl alcohol (PVA) (or another suitable resorbable polymer) that is doped with an ionic solution. Alternatively, sleeve 480 (e.g., substrate 481) could be configured to absorb ions from perilymph in the cochlea in order to become conductive after implantation into a recipient's cochlea. A conductive sleeve 480, in accordance with an embodiment of the invention, may provide less of an impediment to stimulation reaching the cochlea from electrodes 250 covered by sleeve 480. In certain embodiments, sleeve 480 is constructed of a non-resorbable material. In such embodiments, sleeve 480 is either conductive in order to mitigate the effect of sleeve 480 on stimulation, as described above, or configured such that sleeve 480 does not cover any of electrodes 250. For example, in certain non-resorbable embodiments, gap 483 of sleeve 480 may be large enough that sleeve 480 does not cover any of electrodes 250. In such embodiments, gap 483 may also be small enough that sleeve 480 will remain on carrier member 220, or may be secured to carrier member 220 as described below.

Figure 4C:
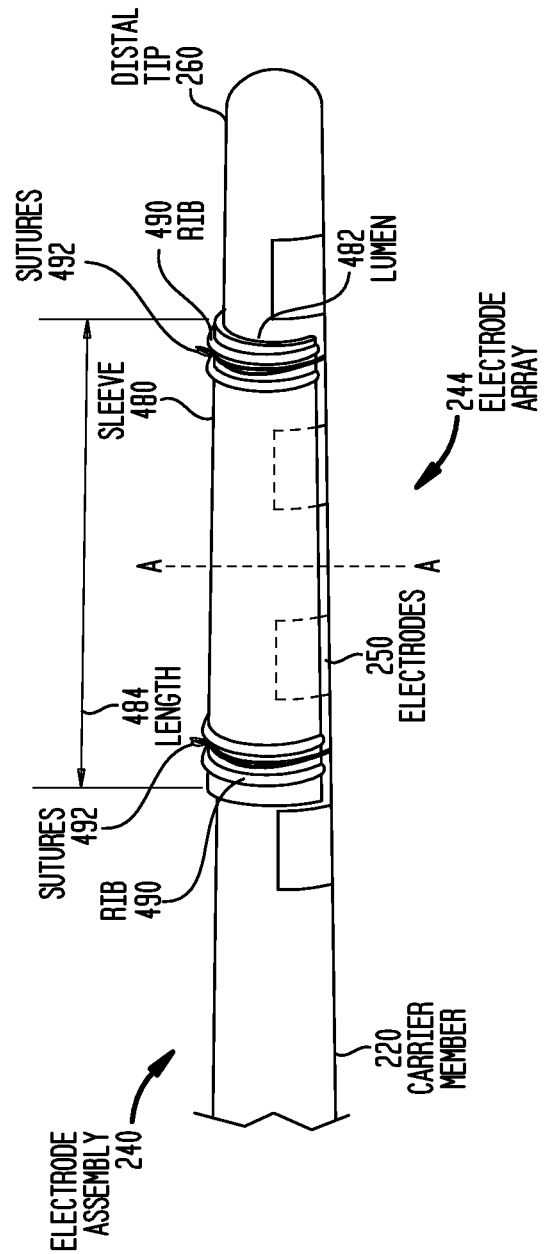
FIG. 4C is a side perspective view of a drug-delivery sleeve disposed on a carrier member, in accordance with embodiments of the present invention.

FIG. 4C is a side perspective view of a drug-delivery sleeve 480 disposed on a carrier member 220, in accordance with embodiments of the present invention. A drug-delivery sleeve in accordance with embodiments of the present invention may be secured to or otherwise retained stationary on carrier member 220 via sutures, in addition to or as an alternative to other methods described above for retaining a drug-delivery sleeve 480 stationary on a carrier member 220 or otherwise retaining a sleeve 480 on a carrier member 220. In some embodiments, a drug-delivery sleeve comprises one or more suture-retaining elements to facilitate the use of sutures to retain a drug-delivery sleeve stationary on a carrier member. In the illustrative embodiment of FIG. 4C, sleeve 480 is shaped with an outer surface comprising a plurality of suture-retention elements, namely ribs 490. A first pair of ribs 490 is disposed at a first end of sleeve 480 and a second pair of ribs 490 is disposed at a second end of sleeve 480. When one or more sutures 492 are applied to sleeve 480 between a pair of ribs 490, respectively, the pairs of ribs 490 retain the suture(s) 492 in place relative to sleeve 480. Such ribs 492 assist in preventing sleeve 480 from slipping out from under suture(s) 492, for example. In alternative embodiments, sleeve 480 may be shaped such that it includes a greater or lesser number of ribs 490 than the four illustrated in FIG. 4C. In some embodiments, sleeve 480 may include ribs 490 that are disposed individually on sleeve 480, and not in pairs. Sutures 492 are preferably used with embodiments in which sleeve 480 is constructed of a non-resorbable material.

Figure 4D:
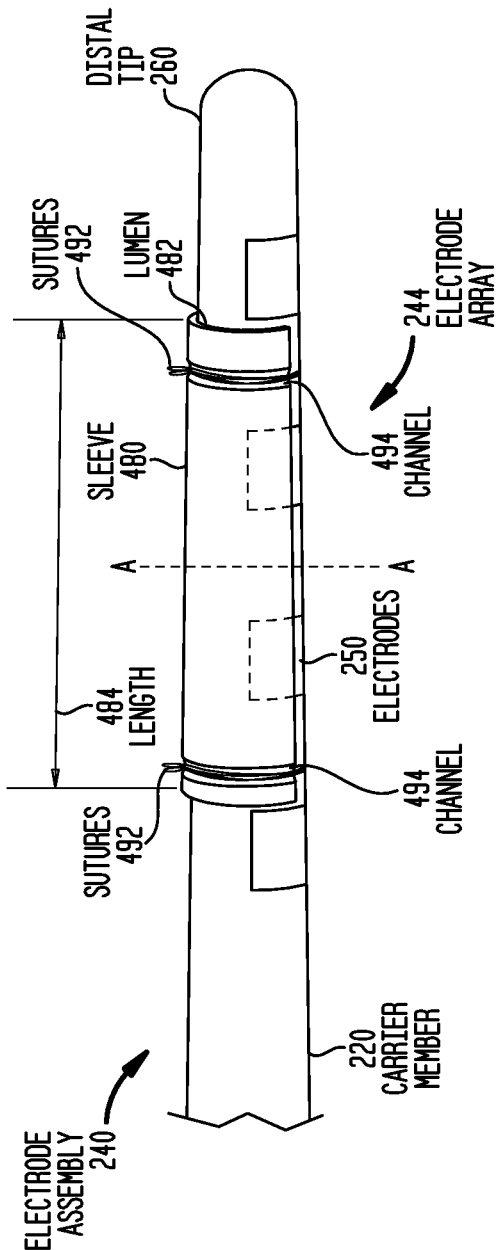
FIG. 4D is a side perspective view of another drug-delivery sleeve disposed on a carrier member, in accordance with embodiments of the present invention.

FIG. 4D is a side perspective view of a drug-delivery sleeve 480 disposed on a carrier member 220, in accordance with embodiments of the present invention. In the illustrative embodiment of FIG. 4D, sleeve 480 is shaped with an outer surface comprising a plurality of channels 494 as suture-retention elements. A first channel 494 is disposed at a first end of sleeve 480 and a second channel 494 is disposed at a second end of sleeve 480. When one or more sutures 492 are applied to sleeve 480 in channels 494, respectively, the channels 494 retain the suture(s) 492 in place relative to sleeve 480. Such channels 494 assist in preventing sleeve 480 from slipping out from under suture(s) 492, for example. In alternative embodiments, sleeve 480 may be shaped such that it includes more a greater or lesser number of channels 494 than the two illustrated in FIG. 4D, and may be disposed at different locations along sleeve 480.

Alternatively, when sleeve 480 is constructed of a non-resorbable material, a sleeve 480 may be secured or otherwise retained stationary on carrier member 220 by a platinum ring that is crimped around sleeve 480. Because the platinum ring is crimped around sleeve 480, the initial geometry of the platinum ring need not be precise, and a single ring size may be used no matter where along carrier member 220 the platinum ring is crimped. Additionally, the platinum ring may be crimped between pairs of ribs 490 shown in FIG. 4C, or in channels 494 shown in FIG. 4D.

FIG. 5A is a side perspective view of a drug-delivery sleeve 580 in accordance with embodiments of the present invention. Drug-delivery sleeve 580 comprises a tubular substrate 581 and a lumen 582 having a lumen diameter 585 (see FIG. 2B), and is similar to drug-delivery sleeve 480 of FIG. 4. However, unlike sleeve 480, sleeve 580 has a substantially circular cross-sectional shape and comprises severable regions 530 at which sleeve 580 may be severed. FIG. 5B is a cross-sectional view of carrier member 220 and sleeve 580 through line A-A of FIG. 5A. As illustrated in FIG. 5B, sleeve 580 has a substantially circular cross-section and is configured to completely surround a circumference of carrier member 220. Alternatively, sleeve 580 may have a substantially C-shaped or a substantially U-shaped cross-section, including a gap similar to gap 483 of sleeve 480, and be configured to at least partially surround a circumference of carrier member 220 (see, e.g., FIGS. 4A and 4B).

Severable regions 530 of sleeve 580 are similar to severable regions 330 illustrated in FIG. 3A and serve as regions at which sleeve 580 may be readily severed. In the embodiment illustrated in FIG. 5A, each severable region 530 includes a thinned region 534 at which less material is present allowing sleeve 580 to be readily cut or torn. Alternatively, each severable region 530 may comprise a plurality of openings, similar to openings 332 of FIG. 3A, around a circumference of sleeve 580. Sleeve 580 may be cut using a suitable cutting tool.

Severable regions 530 increase the options for the application of therapy in a recipient via sleeve 580. Providing sleeve 580 with severable regions 530 allows one or more portions of sleeve 580 to be detached and positioned on carrier member 220. Accordingly, in addition to positioning the entire sleeve 580 on carrier member 220, the option of breaking off and positioning one or more portions of sleeve 580 on carrier member 220 is also available after manufacture of carrier member 220, such as at the time of surgery. This selectability allows the dosage and/or location of therapy to be tailored for a particular recipient after manufacture of the implantable medical device, such as at the time of surgery. In the embodiment illustrated in FIG. 5A, are severable regions 530 are substantially evenly distributed along sleeve 580. In alternative embodiments, severable regions 530 may be located along sleeve 580 such that, when sleeve 580 is positioned on carrier member 220, each severable region 530 is disposed between a pair of adjacent electrodes 250.

Figure 6:
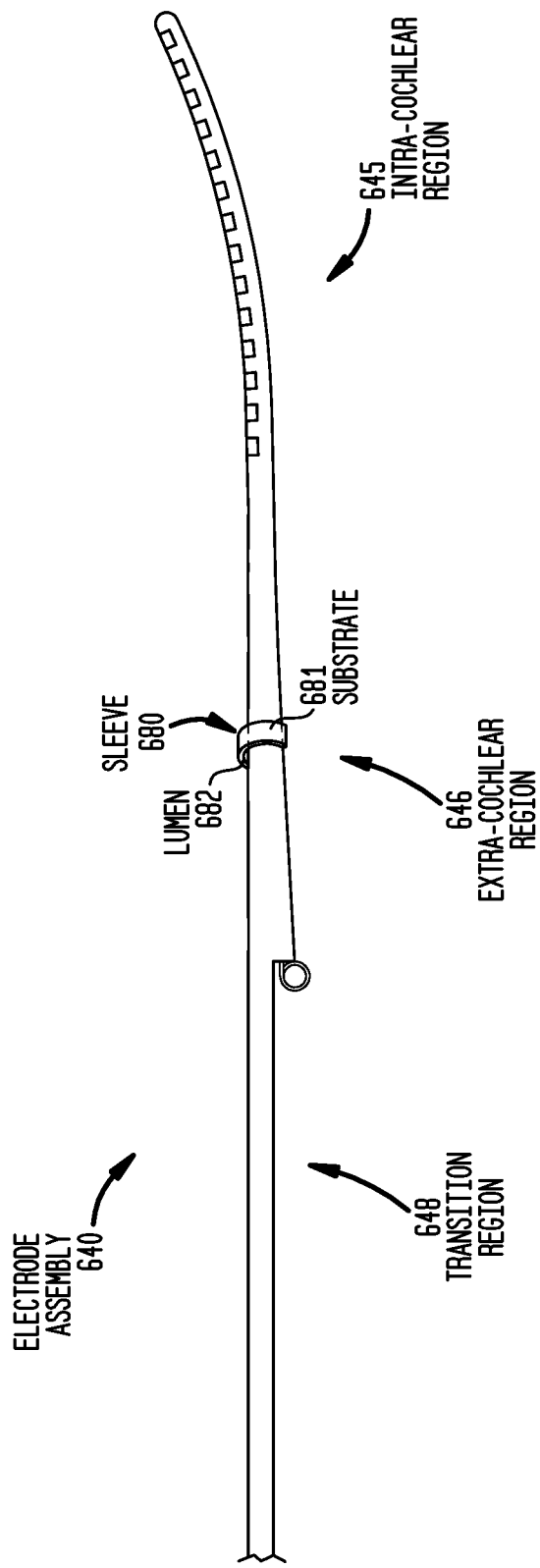
FIG. 6 is a side perspective view of a drug-delivery sleeve attached to an extra-cochlear region of an electrode assembly, in accordance with embodiments of the present invention.

FIG. 6 is a side perspective view of a drug-delivery sleeve 680 attached to an extra-cochlear region 646 of an electrode assembly 640, in accordance with embodiments of the present invention. Electrode assembly 640 is an embodiment of electrode assembly 140 of FIG. 1A and comprises an intra-cochlear region 645 configured to be at least partially inserted into a cochlea of a recipient, an extra-cochlear region 646 configured to be disposed outside of the cochlea after implantation of the intra-cochlear region 645, and a transition region 648 that extends between extra-cochlear region 646 and stimulator unit 134 (see FIG. 1A). Drug-delivery sleeve 680 comprises a tubular substrate 681 and a lumen 682, and is similar to drug-delivery sleeves 280 described above in relation to FIG. 2.

In the illustrative embodiment of FIG. 6, a drug-delivery sleeve 680 is positioned at least partially around a circumference of extra-cochlear region 646. Sleeve 680 may be positioned on extra-cochlear region 646 prior to implantation of electrode assembly 640. In the illustrative embodiment of FIG. 6, sleeve 680 may be longitudinally displaced along extra-cochlear region 646 so that sleeve 680 may be positioned where it will not obstruct a surgeon's view during the insertion of intra-cochlear region 645 at least partially into a recipient's cochlea. Once intra-cochlear region 645 has been inserted, sleeve 680 may be displaced along extra-cochlear region 646 such that it abuts a tissue opening (such as a cochleostomy) through which intra-cochlear region 645 has been inserted. While sleeve 680 abuts the tissue opening, it does not enter the cochlea. Providing a sleeve 680 that may be moved out of view during insertion and subsequently moved to a position abutting a tissue opening allows greater flexibility in the design of sleeve 680. Specifically, because sleeve 680 may be moved out of view during insertion, sleeve 680 may be larger than a permanently placed sleeve that would need to be small enough not to obstruct a surgeon's view during insertion. Additionally, because sleeve 680 may be displaced along electrode assembly 640, it can be moved to a position abutting the tissue opening despite variations in the depth to which intra-cochlear region 645 may be inserted due to, for example, cochlea size and anatomical variations in recipients.

In certain embodiments, sleeve 680 is malleable and may be secured to or otherwise retained stationary on extra-cochlear region 646 by clamping or compressing sleeve 680 to extra-cochlear region 646 once sleeve 680 has been located such that it abuts the tissue opening. Drug-delivery sleeve 680 may be positioned on an electrode assembly of a conventional cochlear implant after manufacture of the cochlear implant.

In certain embodiments, drug-delivery sleeve 680 releasably carries one or more drugs that encourage the sealing of the cochleostomy. For example, a drug that encourages fibrous tissue growth to achieve a faster and stronger cochleostomy seal may be releasably carried by drug-delivery sleeve 680. Encouraging and/or improving the formation of the cochleostomy seal provides a number of benefits to a cochlear implant recipient. For example, as noted above, it has been theorized that a delay in forming a cochleostomy seal can reduce residual hearing. Thus, improving the formation of the cochleostomy seal may help maintain residual hearing following implantation. Additionally, prior to sealing the cochleostomy, the cochleostomy may provide a pathway for pathogens to reach the inner ear. As such, encouraging and/or improving the formation of the cochleostomy seal may reduce the probability of infection reaching the inner ear.

In some embodiments, drug-delivery sleeve 680 (e.g., substrate 681) is constructed of a completely resorbable polymer, such as those listed above in relation to drug-delivery sleeve 280. More specifically, drug-delivery sleeve 680 may be constructed of a polymer configured to be completely resorbed within one to three months after implantation. Additionally, because drug-delivery sleeve 680 is configured to be positioned on extra-cochlear region 646 outside of the cochlea, drug-delivery sleeve 680 may also be used to deliver drugs to a recipient's middle ear in some embodiments. As such, drug-delivery sleeve 680 may releasably carry drugs beneficial to the middle ear in such embodiments. Additionally, in these embodiments, drug-delivery sleeve 680 may be displaced along electrode assembly 640 after insertion of at least a portion of intra-cochlear region 645 to position drug-delivery sleeve 680 at a desired location within the middle ear.

FIG. 7A is a side perspective view of a drug-delivery tip attachment 790 attached to a carrier member 720, in accordance with embodiments of the present invention. Electrode assembly 740, which is an embodiment of electrode assembly 140 of FIG. 1A, comprises carrier member 720 having an electrode array 744 including electrodes 750. Tip attachment 790 comprises a carrier body 791 that releasably carries at least one drug 192 and that may be constructed of a resorbable material or a non-resorbable material. Drug-delivery tip attachment 790 is preferably resiliently flexible. However, the flexibility of tip attachment 790 may be different in alternate embodiments. As used herein, a "resiliently flexible" tip attachment is a tip attachment that will not bend excessively or fold over when exposed to the usual insertion forces applied to insert a distal portion of an electrode assembly into a recipient's cochlea.

Prior to inserting electrode assembly 740 into a cochlea of a recipient, drug-delivery tip attachment 790 may be attached to carrier member 720. In the illustrative embodiment of FIG. 7A, tip attachment 790 is mechanically attached to carrier member 720. FIG. 7B is a cross-sectional view of electrode assembly 740 and tip attachment 790 of FIG. 7A. FIG. 7C is a cross-sectional view of electrode assembly 740 and tip attachment 790 of FIG. 7A along a line A-A of FIG. 7A. In the embodiment illustrated in FIG. 7B, carrier member 720 has an atypical distal tip 760. More specifically, carrier member 720 has a bulbous distal tip 760 that is configured to be attached to tip attachment 790 via a non-bonded retention means (e.g., compression retention, interference retention) within an aperture 792, which is a recess in tip attachment 790. In certain embodiments, distal tip 760 may be constructed of silicone. The silicone may provide a relatively high amount of static friction to enhance the strength of the attachment of distal tip 760 to tip attachment 790.

In the illustrative embodiment of FIGS. 7A-7C, tip attachment 790 includes opposing top and bottom surfaces 796 and 794, as well as opposing front and rear surfaces 798 and 699. Aperture 792 extends from a central portion of tip attachment 790 out of a portion of bottom surface 794 and a portion of a rear surface 799 of tip attachment 790. Tip attachment 790 may be attached to carrier member 220 by pressing tip attachment onto carrier member 720 such that aperture 792 receives distal tip 760. For example, the portion of aperture 792 in bottom surface 794 of tip attachment 790 may be positioned over distal tip 760. Then, leading with bottom surface 794, tip attachment 790 may be pressed over distal tip 760. Tip attachment 792 may be secured to distal tip 760 via an interference or friction fit, or the like. FIGS. 7A-7C show one example of how a tip attachment in accordance with embodiments of the invention may be attached to an electrode assembly. However, a tip attachment in accordance with embodiments of the present invention may be mechanically attached to an electrode assembly in any suitable manner.

FIG. 8A is a side perspective view of a drug-delivery tip attachment 890 attached to a carrier member 220, in accordance with embodiments of the present invention. FIG. 8B is a cross-sectional view of electrode assembly 240 and tip attachment 890 of FIG. 8A. Tip attachment 890 comprises a carrier body 891 and is similar to tip attachment 890, except that the recess in tip attachment 890 is a cavity 892 having a different configuration than aperture 792. Additionally, tip attachment 890 is configured to be bonded to carrier member 220 rather than mechanically attached to a carrier member like tip attachment 790. In one embodiment, such bonding is performed in a sterile field immediately prior to surgery. In another embodiment, such bonding is performed during manufacturing, such as at one of the last few steps of manufacturing.

In one embodiment, the above bonding is performed by disposing a glue layer on one or more of cavity 892 and distal tip 260 and pressing together cavity 892 and distal tip 260 prior to surgery. This may be performed manually or with a simple press-tool that aligns the two components and presses them together with a predefined amount of pressure. Alternatively, a liquid glue may be applied between cavity 892 and distal tip 260. In one preferred embodiment, the liquid glue sets and/or cures rapidly. In another embodiment, a UV-cured glue is pre-applied to cavity 892 and/or distal tip 260, or is applied as a liquid, or is a separate component that is inserted between cavity 892 and distal tip 260. In one embodiment, a liquid perfluoropol polymer such as that described in International Application WO 2007/021620 A2 may be utilized. Other adhesives include, but are not limited to, fibrin glues, cyanoacrylates, polyurethane adhesives, silicone adhesives, and UC-cured acrylics. In another embodiment, chemical surface modification may be utilized to attain a desired bonding. For example, in one embodiment, covalently bonded proteins, or sulfonation may be performed to increase the wetability of the surface.

A drug-delivery tip attachment, in accordance with embodiments of the present invention, may be manufactured separately from, for example, a carrier member of an implantable medical device, and may be positioned on the carrier member subsequent to the carrier member's manufacture or sterilization. Providing independently-manufactured and physically distinct (i.e., "separate") drug-delivery tip attachments in accordance with embodiments of the present invention increases flexibility for the application of therapy. In certain embodiments, separate drug-delivery tip attachments releasably carrying different types of drugs are provided, allowing the type of drug to be applied to be selected after manufacture of the implantable device, such as at the time of surgery, as described above in relation to drug-delivery sleeves of embodiments of the present invention. Drug-delivery tip attachments of certain embodiments of the present invention are configured to be attached to a distal tip of a carrier member. As such, these drug-delivery tip attachments are not appropriate drug-delivery accessories for delivering to a cochleostomy drugs beneficial for the formation of a cochleostomy seal. However, because the distal tip of a carrier member may be positioned in a more apical region of a recipient's cochlea relatively distant from the cochleostomy, drug-delivery tip attachments attached to the distal tip may carry drugs that are detrimental to the formation of a cochleostomy seal. Also, in certain embodiments, separate drug-delivery tip attachments having different dosages may be provided, allowing the dosage of the drug(s) to be selected after manufacture of the implantable device. For example, drug-delivery tip attachments releasably carrying different amounts of a drug may be provided.

Like drug-delivery sleeves 280 described above, drug-delivery tip attachments in accordance with embodiments of the present invention may be constructed of a resorbable material or a non-resorbable material. Completely resorbable drug-delivery tip attachments, in accordance with embodiments of the present invention, provide particular benefits for carrier members inserted in the cochlea using an Advance Off-Stylet™ (AOS) mode of implantation since the tip attachment is required during insertion, but is not required once insertion is complete. In the AOS mode of implantation, the carrier member with a stylet inserted therein is inserted through a cochleostomy until the tip attachment is positioned just short of the basal turn of the cochlea. Once the tip attachment has reached this position, the carrier member may be advanced or moved off the stylet and further into the scala tympani. As the carrier member is advanced off the stylet, the carrier member is also free to begin to adopt its pre-formed spiral curvature.

If a carrier member without the tip attachment of the present invention is too far from the modiolus as the carrier member advances off the stylet, a distal region of the carrier member may curl or fold over upon itself such that electrodes in the distal region face one another. This may occur when inserting a carrier member having a distal region with a radius of curvature that is less than half of the width of the scala timpani proximate the first basal turn of the cochlea. The carrier member will then continue to be implanted with this improper configuration. The tip attachment of the present invention helps to prevent such foldover of the carrier member as the carrier member is moved off the stylet in the AOS mode of implantation. The tip attachment of the present invention is not pre-curved and therefore does not have the same tendency to fold over. In addition, the tip attachment extends the length of the distal region of the carrier member. This additional length is configured to catch on the modiolus as the carrier member curls to prevent the carrier member from folding over on itself, as described above.

Once the elongate component has reached its desired final insertion position in the cochlea, the additional length of the tip attachment of the present invention will press against an outer wall of the cochlea and hold electrodes carried by the carrier member off the inner wall of the cochlea. Because it is preferable to position the electrodes as close to the inner wall as possible, this implantation orientation is not ideal. However, once the resorbable tip attachment is completely resorbed, the tip attachment is no longer be present to hold the electrodes off the inner wall, and the carrier member will position the electrodes closer to the inner wall.

The types of drugs that may releasably carried by drug-delivery accessories in accordance with embodiments of the present invention include anti-inflammatories (e.g., dexamethasone, cortisol, prednisolone, triamcinolone), neurotrophic factors (e.g., nerve growth factor (NGF), fibroblast growth factor (FGF), brain-derived neurotrophic factor (BDNF), glial cell-derived neurotrophic factor (GDNF), neurotrophin-3 (NT-3), neurotrophin-4 (NT-4), leukaemia inhibitory factor (LIF), transforming growth factor (TGF)), antimicrobials (e.g., chitosan, silver ions, PEG, cationic peptides), antioxidants (e.g., ascorbic acid (vitamin C), glutathione (including N-acetyl-L cysteine), lipoic acid, alpha-tocopherol (vitamin E), ubiquinol as well as any synthetic analogues), antibiotics (e.g., amikacin, ciprofloxacin) and other drugs found to be beneficial for the health of the cochlea (e.g., salicylates, dizocilpine (MK801)).

Of the drugs listed above, the preferred antibiotic drug for application at a cochleostomy site is ciprofloxacin, and the preferred anti-inflammatory drug for application in the intra-cochlear region is dexamethasone. Additionally, neurotrophic factors, such as those listed above, may be beneficially applied to actively prevent the loss of spiral ganglion cells to potentially improve the performance of a cochlear implant.

It is to be understood that any suitable amount of a drug may be releasably carried in a drug-delivery accessory of the present invention. Additionally, drug-delivery accessories in accordance with embodiments of the present invention may have various drug-delivery profiles.

In addition, embodiments of the present invention may be used for direct intra-cochlear drug delivery, which has significant potential advantages. For example, direct intra-cochlear drug delivery bypasses the blood-cochlea barrier allowing drugs to reach their intended targets more directly and utilizing lower doses of the drugs and less generalized application of drugs in the recipient. Additionally, drugs released into the perilymph compartment of the scala tympani may readily access the hair cells and the synaptic regions of the hair cells located in that area.

It is to be understood that one or more drugs may be disposed on or in a portion or substantially all of each drug-delivery accessory depending on the particular application. For example, it may be beneficial for a drug-delivery accessory to have a drug disposed in only a portion of the accessory, with the remaining portion of the accessory configured as a carrier or supporting member for delivery of the bioactive substance to the recipient.

Embodiments of the drug-delivery accessory of the present invention may be constructed as a woven mesh. In such embodiments, the threads of the woven mesh may be treated with one or more drugs during the fabrication of the mesh, or the mesh may be treated with one or more drugs subsequent to fabrication and prior to implantation with the implantable medical device.

According to a further embodiment of the present invention, the drug-delivery accessory may be constructed of a polymeric material, in which molecules or other components of a drug disposed are within the chemical structure of the drug-delivery accessory. One example of a polymeric material that may be used to construct an embodiment of a drug-delivery accessory of the present invention is silicone. One or more drugs may be disposed within the silicone drug-delivery accessory such that the drug(s) are released from the drug-delivery accessory.

In another embodiment, the drug-delivery accessory is configured to be bonded to the surface of the implantable medical device thereby eliminating the space or gap that may form between the drug-delivery accessory and the adjacent surface of the medical device component. The reduction and/or elimination of this gap reduces or eliminates the likelihood of bacterial growth between the two. In one embodiment, such bonding is performed in a substantially sterile field immediately prior to surgery. Alternatively, such bonding is performed after the medical device is implanted in the patient. In another embodiment, such bonding is performed during manufacturing, such as at one of the last few steps of manufacturing. In one embodiment, the bonding described above may be performed in a manner similar to any one of those described above in relation to the illustrative embodiment of FIG. 8.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. For example, in the description of the exemplary embodiments described above, the drug-delivery assembly is applied to a carrier member of a cochlear implant. It should be appreciated, however, that embodiments of the drug-delivery assembly of the present invention may be applied to other types of elongate components of implantable medical device. More broadly, aspects of the present invention may be implemented in implantable catheters. The present embodiments are, therefore, to be considered in all respects as illustrative and not restrictive. All patents and publications discussed herein are incorporated in their entirety by reference thereto.

What is claimed is:

1. An implantable medical device comprising:
an elongate component that is at least partially implantable in a cochlear of a recipient; and
a drug-delivery sleeve releasably carrying at least one drug and having a lumen configured to receive the elongate component so as to allow relative displacement of the sleeve and the elongate component, wherein the sleeve is manually compressible to the elongate component such that the sleeve is retained stationary relative to the elongate component at an intra-cochlear region of the elongate component, wherein the sleeve includes an attachment frame having a length extending between first and second ends of the sleeve, and a plurality of rings each connected to the attachment frame, wherein the rings are aligned along the length of the attachment frame such that the elongate component is positionable in respective lumens of each of the rings concurrently, and wherein the attachment frame comprises a plurality of severable regions at which the rings may be severed from each other.

2. The device of claim 1, wherein the implantable medical device is a cochlear implant and the elongate component is an elongate carrier member having a plurality of electrodes longitudinally spaced along the carrier member.

3. The device of claim 2, wherein the sleeve is resorbable and at least partially covers each of the plurality of the electrodes.

4. The device of claim 2, wherein the sleeve is a ring having a length that is less than or equal to a distance between two adjacent electrodes of the plurality of electrodes.

5. The device of claim 1, wherein the elongate component includes an extra-cochlear region, wherein the lumen is configured so as to allow relative displacement of the sleeve relative to the intra-cochlear and extra-cochlear regions, and wherein the sleeve is manually compressible to the intra-cochlear and extra-cochlear regions such that the sleeve is retained stationary relative to the elongate component.

6. The device of claim 1, wherein the sleeve comprises at least one mechanical weakness at which a first portion of the sleeve may be detached from a second portion of the sleeve.

7. The device of claim 1, wherein the elongate component is tapered and a diameter of the elongate component at a desired position is greater than or equal to a diameter of the lumen at the desired position.

8. The device of claim 1, wherein the sleeve is configured to substantially surround a circumference of the elongate component when the elongate component is disposed in the lumen.

9. The device of claim 8, wherein the sleeve comprises a gap along its length such that the sleeve surrounds less than all of a circumference of the elongate component when the elongate component is disposed in the lumen.

10. The device of claim 1, further comprising a second drug-delivery sleeve releasably carrying at least one drug and having a lumen configured to receive the elongate component so as to allow relative displacement of the sleeve and the elongate component.

11. An implantable medical device comprising:
an elongate tapered electrode carrier member that is implantable in a recipient;
a tubular substrate having a lumen extending between first and second ends of the substrate, wherein the lumen is configured to receive the electrode carrier member so as to allow relative displacement of the substrate and the electrode carrier member, wherein the substrate is shaped so as to be retained stationary at a desired position along the electrode carrier member at an intra-cochlear region of the electrode carrier member, wherein the lumen has a first diameter at the first end and a second diameter at the second end that is smaller than the first diameter, and wherein the substrate is positioned on the electrode carrier member such that the first diameter of the lumen is disposed at the desired position and the second diameter of the lumen is disposed at a portion of the electrode carrier member having a diameter that is greater than or equal to the second diameter of the lumen, and wherein the diameter of the electrode carrier member at the desired position is greater than or equal to the diameter of the lumen at the desired position; and
a drug releasably carried by the substrate.

12. The device of claim 11, wherein an outer surface of the substrate comprises one or more suture-retention elements configured to prevent relative displacement of the substrate and the electrode carrier member when a suture is positioned around the substrate with sufficient tightness in or between the one or more suture-retention elements.

13. The device of claim 12, wherein the one or more suture-retention elements are two ribs disposed at lease partially around the substrate and configured to retain a suture between the two ribs, or a channel disposed around the substrate and configured to receive the suture.

14. The device of claim 11, wherein the substrate is configured to substantially surround a circumference of the electrode carrier member when the electrode carrier member is disposed in the lumen.

15. The device of claim 14, wherein the substrate comprises a gap along its length such that the substrate surrounds less than all of a circumference of the electrode carrier member when the electrode carrier member is disposed in the lumen.

16. The device of claim 15, further comprising:
an ionic solution disposed within the substrate such that the substrate is electrically conductive.

17. The device of claim 15, wherein the substrate is configured such that, when inserted into a cochlea of a recipient, the substrate absorbs ions from the recipient's cochlear fluid.

18. The device of claim 11, wherein the implantable medical device is a cochlear implant.

19. The device of claim 11, wherein the electrode carrier member has a plurality of electrodes longitudinally spaced along the carrier member.

20. The device of claim 19, wherein the substrate at least partially covers each of a plurality of the electrodes.

21. The device of claim 19, wherein the substrate is a ring having a length that is less than or equal to a distance between two adjacent electrodes of the plurality of electrodes.

* * * * *